US012440255B2

(12) United States Patent
Elsawah et al.

(10) Patent No.: US 12,440,255 B2
(45) Date of Patent: Oct. 14, 2025

(54) BONE SCREW INSERTERS AND METHODS

(71) Applicant: Medos International Sarl, Le Locle (CH)

(72) Inventors: Lamis Elsawah, King of Prussia, PA (US); Shawn Harris, Dighton, MA (US); Thomas Runco, Providence, RI (US); William Miller, Middleboro, MA (US); Michael Sorrenti, Middleboro, MA (US); Eric Biester, Barrington, RI (US); Brad Schertle, Glen Arm, MD (US)

(73) Assignee: Medos International Sárl, Le Locle (CH)

( * ) Notice: Subject to any disclaimer, the term of this patent is extended or adjusted under 35 U.S.C. 154(b) by 0 days.

(21) Appl. No.: 17/982,096

(22) Filed: Nov. 7, 2022

(65) Prior Publication Data

US 2023/0141374 A1 May 11, 2023

Related U.S. Application Data

(60) Provisional application No. 63/277,153, filed on Nov. 8, 2021.

(51) Int. Cl.
*A61B 17/88* (2006.01)

(52) U.S. Cl.
CPC ................................ *A61B 17/8883* (2013.01)

(58) Field of Classification Search
CPC .............. A61B 17/8875; A61B 17/888; A61B 17/8883; A61B 17/8886; A61B 17/8891
See application file for complete search history.

(56) References Cited

U.S. PATENT DOCUMENTS 6,554,834 B1 4/2003 Crozet et al.
7,087,057 B2 8/2006 Konieczynski et al.
(Continued)

FOREIGN PATENT DOCUMENTS

CN 203042419 U 7/2013
EP 1234637 B1 3/2008
(Continued)

OTHER PUBLICATIONS

International Search Report and Written Opinion, Application No. PCT/EP2022/081152; dated May 15, 2023; 21 pages.
(Continued)

*Primary Examiner* — Nicholas W Woodall
(74) *Attorney, Agent, or Firm* — Barnes & Thornburg LLP

(57) ABSTRACT

Bone screw drivers are disclosed that apply torque to a threaded shank of a bone screw assembly and receive a cement delivery device to introduce bone cement through the threaded shank. Also disclosed are driver adapters that couple to a driver in order to facilitate application of torque thereto. The driver adapter can decouple from the driver after implanting a bone screw shank to allow the subsequent use of a cement delivery device in combination with the driver. The devices can be reusable and can employ a number of additional components, including retaining and counter-torque sleeves, driving handles, etc. Further, the devices can allow setup of a bone screw inserter assembly outside a surgical field, such that a completed assembly can be passed to a surgeon or other user for immediate use.

19 Claims, 28 Drawing Sheets

(56) References Cited

U.S. PATENT DOCUMENTS

| | | | | |
|---|---|---|---|---|
| 7,354,442 | B2 | 4/2008 | Sasso et al. | |
| 7,824,412 | B2 | 11/2010 | Falahee | |
| 8,100,916 | B2 | 1/2012 | Kumar et al. | |
| 8,366,717 | B1 | 2/2013 | Jordan et al. | |
| 8,764,806 | B2 | 7/2014 | Abdou | |
| 9,084,647 | B2 | 7/2015 | Suh | |
| 9,155,580 | B2 | 10/2015 | Cormier et al. | |
| 9,265,548 | B2 | 2/2016 | Jones et al. | |
| 9,345,464 | B2 | 5/2016 | Abdou | |
| 9,433,436 | B2 | 9/2016 | Schon et al. | |
| 9,554,909 | B2 | 1/2017 | Donner et al. | |
| 9,572,605 | B2 | 2/2017 | Shipp | |
| 9,675,389 | B2 | 6/2017 | Abdou | |
| 9,687,285 | B2 | 6/2017 | Robinson | |
| 10,039,578 | B2 | 8/2018 | Anderson et al. | |
| 10,299,839 | B2 | 5/2019 | Sicvol et al. | |
| 10,349,986 | B2 | 7/2019 | Wall et al. | |
| 10,463,402 | B2 | 11/2019 | Biester et al. | |
| 10,543,107 | B2 | 1/2020 | Abdou | |
| RE47,871 | E | 2/2020 | Jones et al. | |
| 10,595,912 | B2 | 3/2020 | Krause et al. | |
| 10,610,380 | B2 | 4/2020 | Abdou | |
| 10,856,924 | B2 * | 12/2020 | Rippe | B25B 23/101 |
| 10,857,004 | B2 | 12/2020 | Abdou | |
| 10,888,363 | B2 | 1/2021 | Greenhalgh et al. | |
| 10,893,910 | B2 | 1/2021 | Elliott et al. | |
| 10,932,841 | B2 | 3/2021 | Grizzard et al. | |
| 10,980,574 | B2 | 4/2021 | Konieczynski et al. | |
| RE48,870 | E | 1/2022 | Jones et al. | |
| 11,786,278 | B2 * | 10/2023 | Gladieux | A61B 17/7082 606/86 A |
| RE50,403 | E | 4/2025 | Jones et al. | |
| 2005/0015059 | A1 | 1/2005 | Sweeney | |
| 2005/0131408 | A1 | 6/2005 | Sicvol et al. | |
| 2005/0131421 | A1 | 6/2005 | Anderson et al. | |
| 2007/0299450 | A1 | 12/2007 | Her et al. | |
| 2008/0249530 | A1 | 10/2008 | Truckai et al. | |
| 2009/0138044 | A1 | 5/2009 | Bergeron et al. | |
| 2009/0264895 | A1 | 10/2009 | Gasperut et al. | |
| 2012/0203287 | A1 | 8/2012 | Arambula et al. | |
| 2012/0203288 | A1 | 8/2012 | Lange et al. | |
| 2014/0018816 | A1 | 1/2014 | Fenn et al. | |
| 2014/0257410 | A1 | 9/2014 | Biedermann et al. | |
| 2015/0150683 | A1 | 6/2015 | Donner et al. | |
| 2015/0201985 | A1 * | 7/2015 | Rampersaud | A61B 17/8875 606/86 A |
| 2015/0250521 | A1 * | 9/2015 | Poker | A61B 17/7037 606/104 |
| 2016/0296266 | A1 * | 10/2016 | Chandanson | B25B 23/0035 |
| 2017/0100116 | A1 | 4/2017 | Erramilli et al. | |
| 2017/0367748 | A1 | 12/2017 | Plotkin | |
| 2018/0132918 | A1 | 5/2018 | Insley et al. | |
| 2018/0235684 | A1 | 8/2018 | Hawkes et al. | |
| 2019/0029736 | A1 * | 1/2019 | Wall | A61B 34/20 |
| 2019/0029737 | A1 * | 1/2019 | Wall | A61B 17/8886 |
| 2019/0059967 | A1 | 2/2019 | Chandanson et al. | |
| 2019/0151003 | A1 | 5/2019 | Ackermann et al. | |
| 2019/0216516 | A1 | 7/2019 | Vogt et al. | |
| 2020/0038646 | A1 | 2/2020 | Sweeney et al. | |
| 2020/0085474 | A1 | 3/2020 | Harshman et al. | |
| 2020/0121396 | A1 | 4/2020 | Elliott et al. | |
| 2020/0121398 | A1 | 4/2020 | Elliott et al. | |
| 2020/0170690 | A1 | 6/2020 | Krause et al. | |
| 2020/0337744 | A1 | 10/2020 | Grizzard et al. | |
| 2021/0059724 | A1 * | 3/2021 | Rezach | A61B 17/7002 |

FOREIGN PATENT DOCUMENTS

| | | | |
|---|---|---|---|
| EP | 2745789 | B1 | 4/2017 |
| WO | 2001026568 | A1 | 4/2001 |
| WO | 2009015100 | A2 | 1/2009 |
| WO | 2019246556 | A1 | 12/2019 |
| WO | 2020257276 | A1 | 12/2020 |

OTHER PUBLICATIONS

MEDACTA Unconstrained Screw Technology—Fenestrated Screws, Jun. 2015 (16 pages).

Applicant SRT P/N 698342926 dated Aug. 2017 (1 page).

Applicant SRT P/N 698343194 dated Jul. 2018 (1 page).

Stryker Mantis Redux Surgical Technique, 2011 (40 pages).

Zhiwei He et al., “Bone Cements for Percutaneous Vertebroplasty and Balloon Kyphoplasty: Current Status and Future Developments,” Journal of Orthopaedic Translation (2015) 3, 1-11, Dec. 12, 2014 (11 pages).

* cited by examiner

FIG. 7A
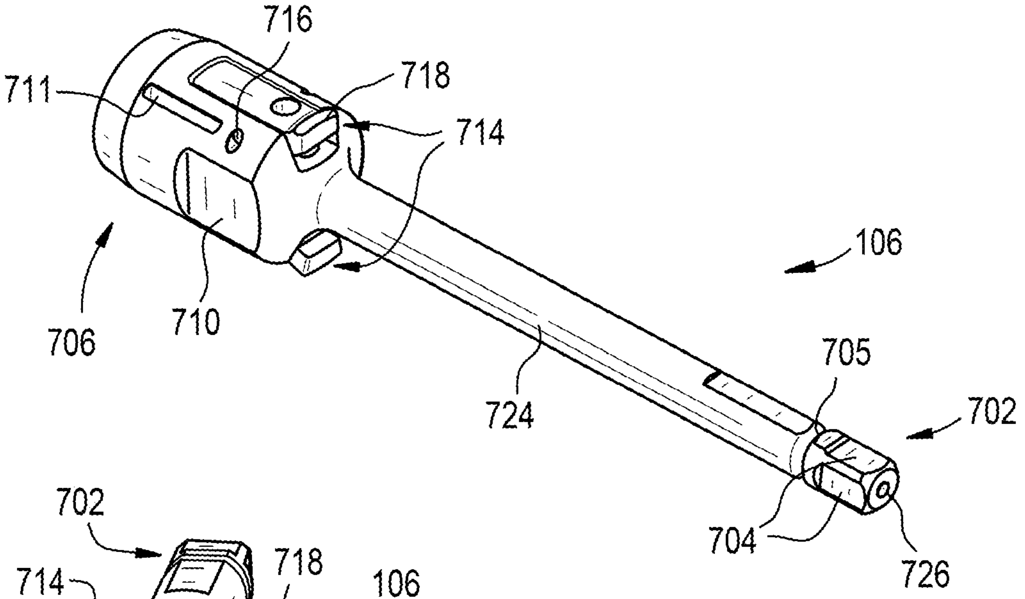
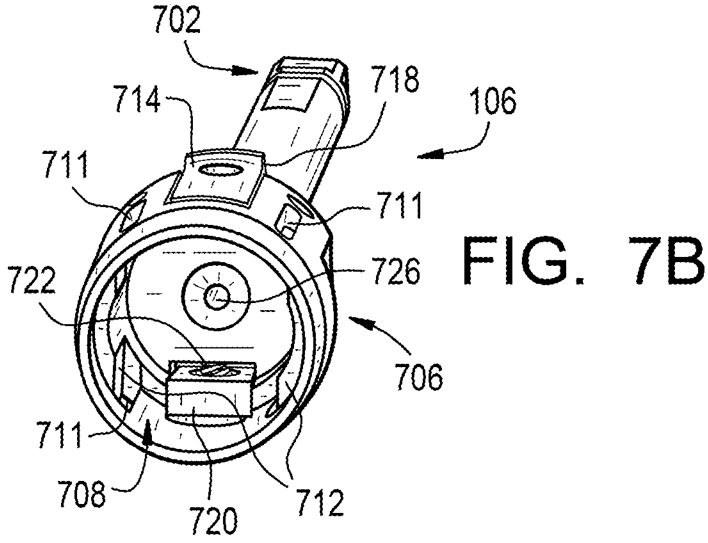
FIG. 7B
FIG. 7C
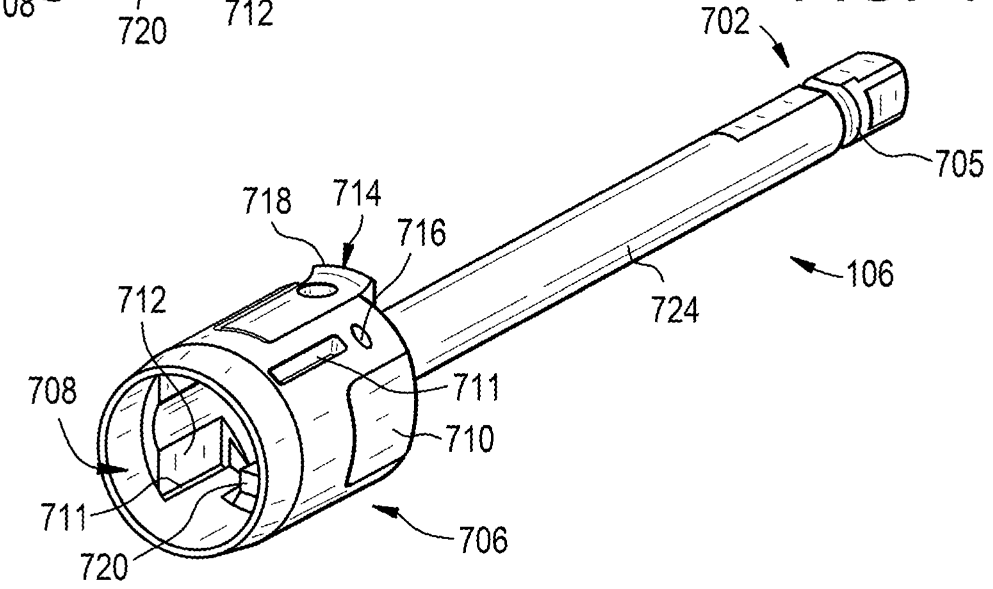

FIG. 27A
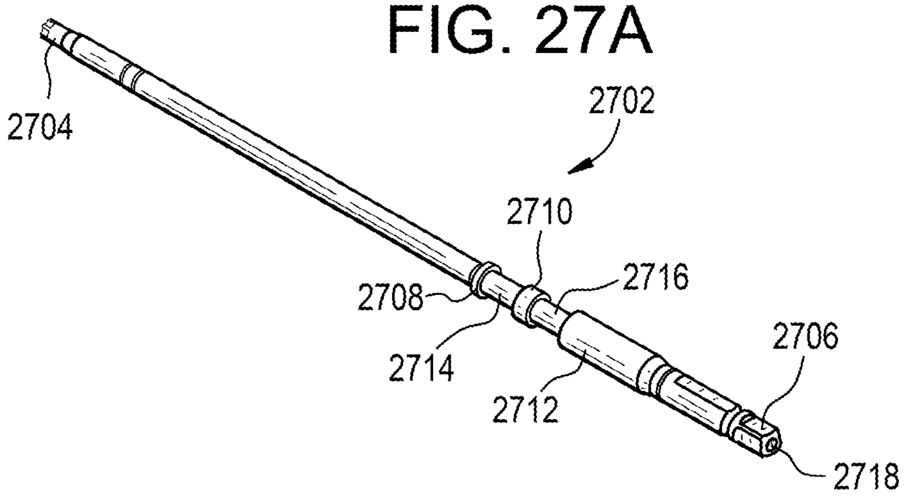
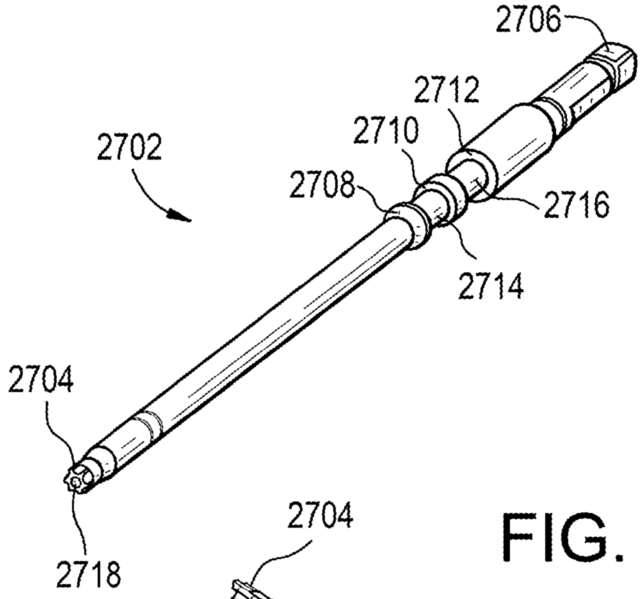
FIG. 27B
FIG. 28
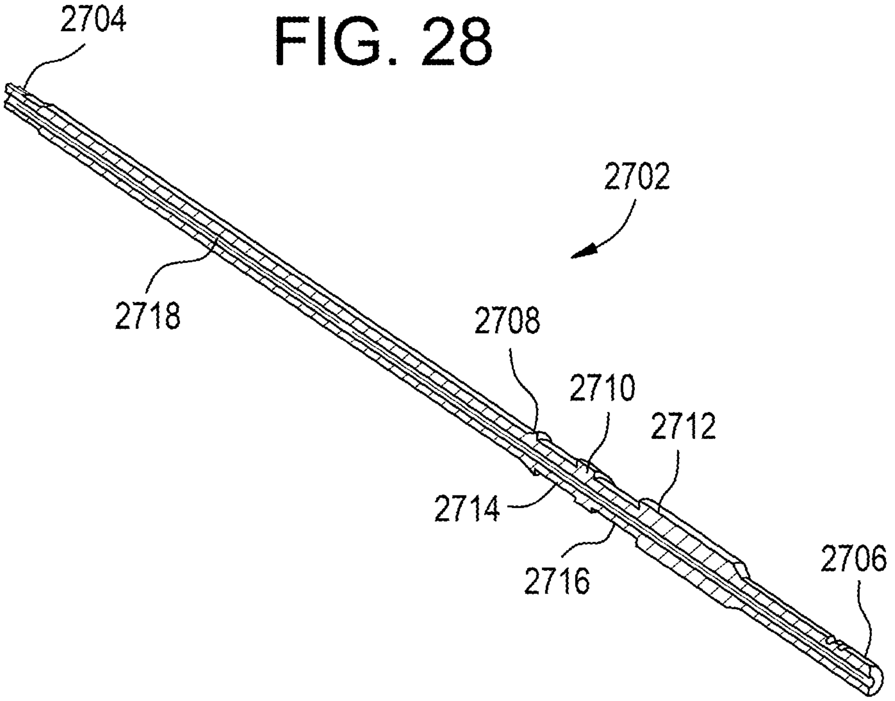

BONE SCREW INSERTERS AND METHODS

CROSS-REFERENCE TO RELATED APPLICATIONS

This application claims the benefit of U.S. Provisional Application No. 63/277,153, filed on Nov. 8, 2021. The entire content of this application is hereby incorporated by reference in its entirety.

FIELD

This disclosure relates generally to surgical instruments and, more particularly, to devices and methods that can be utilized for delivery of bone screws or other implantable assemblies.

BACKGROUND

Bone anchor assemblies can be used in orthopedic surgery to fix bone during healing, fusion, or other processes. In spinal surgery, for example, bone anchor assemblies can be used to secure a rod or other spinal fixation element to one or more vertebrae to rigidly or dynamically stabilize the spine. Bone anchor assembly implantation can require the use of specialized drivers to advance a threaded shank component into bone.

In some cases, fenestrated bone anchor assemblies can be utilized in combination with the delivery of bone cement or other flowable materials to aid in setting and/or securing the component driven into bone. Fenestrated bone anchor assemblies can include a threaded shank having a lumen extending at least part of its length with a distal and/or side opening to allow flowable material to escape from the lumen.

Fenestrated bone anchor assemblies can require specific alignment guides to enable delivery of cement or other flowable material. In some cases an alignment guide can be configured to drive in a screw in addition to receive a cement delivery device. In such prior devices, however, a combined device is often considered single-use and/or lacks compatibility or consistency with other pre-existing hardware.

Moreover, in many cases the use of prior driver and cement delivery devices has required the performance of device setup in the surgical field. It can be advantageous to minimize assembly operations required in the surgical field and enable, for example, setup of an assembly at a "back table" away from the immediate surgical field that can be passed to a surgeon or other user in a ready-to-use configuration.

Accordingly, there is a need for improved instrumentation for use in inserting bone screw assemblies and delivering bone cement or other flowable materials thereto. There is a need for such improved instrumentation that address shortcomings of prior designs, e.g., providing a reusable insertion device capable of delivering flowable materials, working with pre-existing cement delivery devices, permits assembly outside a surgical field, etc.

SUMMARY

The present disclosure provides bone screw inserters and methods that address shortcomings in prior designs and provide unique advantages. Generally speaking, the devices disclosed herein can include bone screw drivers configured to apply torque to a threaded shank of a bone screw assembly and implant it into bone, as well as receive a cement delivery device to introduce bone cement or other flowable material through the threaded shank. Also disclosed are driver adapters that can be coupled to a driver in order to facilitate application of torque thereto during bone screw implantation. The driver adapter can be configured to accommodate a configuration of the driver necessary for coupling with a cement delivery device and can be configured to decouple or release from the driver after implanting a bone screw shank into bone in order to allow the subsequent use of a cement delivery device in combination with the driver. The disclosed drivers and driver adapters can be reusable and can employ a number of additional components to form various assemblies, including retaining and counter-torque sleeves, driving handles, etc. Further, the devices disclosed herein can be utilized in a manner that allows setup of a bone screw inserter assembly outside a surgical field, such that a completed assembly can be passed to a surgeon or other user for immediate use in driving a bone screw assembly into bone.

In one aspect, a surgical assembly is disclosed that includes a driver having a distal tip configured to couple with another component in a manner that prevents rotation therebetween, and a proximal driver body with a lumen extending from the proximal-most end of the driver to the distal-most end of the driver. The surgical assembly further includes a driver adapter having a distal adapter body and a proximal torque-receiving end. The driver adapter is coupled to the driver such that a portion of the proximal driver body is received within a distal-facing cavity of the distal adapter body. The driver adapter is also configured to impart rotational force to the driver and the distal adapter body includes a lock configured to prevent axial separation of the driver and the driver adapter.

Any of a variety of alternative or additional features can be included and are considered within the scope of the present disclosure. For example, in some embodiments, the driver adapter can include a lumen extending from a proximal-most end of the driver adapter to the distal-facing cavity. In certain embodiments, the lock can include one or more pivoting latches that interface with a groove formed on the driver. In some embodiments, the driver can include one or more flats formed on the proximal driver body that interface with one or more flats formed on an interior surface of the distal-facing cavity of the driver adapter.

In some embodiments, the surgical assembly can further include a retaining sleeve disposed over a portion of the driver. In certain embodiments, the retaining sleeve can include a threaded distal end configured to interface with a bone screw receiver head. Moreover, in some embodiments, the retaining sleeve can include a lock configured to prevent separation of the retaining sleeve and driver. The surgical assembly can further include a second sleeve disposed over a portion of the retaining sleeve. In some embodiments, the second sleeve can include a plurality of rigid extensions formed at a distal end thereof configured to be received between portions of a bone screw receiver head. In certain embodiments, the second sleeve can include a plurality of flexible extensions formed at a proximal end thereof configured to deflect and ride over one or more surface features formed on the retaining sleeve. The second sleeve can be configured to move between a distal position, in which the second sleeve is locked against rotation relative to a bone screw receiver head coupled to the retaining sleeve, and a proximal position, in which the second sleeve can rotate relative to the bone screw receiver head coupled to the retaining sleeve.

In some embodiments, the surgical assembly can include a driver handle coupled to the proximal torque-receiving end of the driver adapter. In certain embodiments, a surgical navigation array can be coupled to the driver adapter.

In another aspect, a surgical method is provided that includes inserting a driver through a lumen of a retaining sleeve such that a tip formed at a distal-most end of the driver interfaces with a drive feature formed on a shank of a bone screw assembly. The method further includes coupling the retaining sleeve to a receiver head of the bone screw assembly, and coupling a driver adapter to the driver such that a proximal portion of the driver is received within a distal-facing cavity of the driver adapter and the driver adapter is locked against axial separation from the driver. The method further includes rotating the driver adapter to impart corresponding rotation of the driver and the shank of the bone screw assembly.

The methods disclosed herein can include any of a variety of additional or alternative steps that are considered within the scope of the present disclosure. In some embodiments, for example, the method can further include coupling a driver handle to a proximal end of the driver adapter. In certain embodiments, the method can further include locking the driver against axial separation from the retaining sleeve. In some embodiments, rotation of the driver and the shank of the bone screw assembly can be relative to the retaining sleeve.

In some embodiments, the method can further include inserting the retaining sleeve through a lumen of a second sleeve. The method may further include inserting the retaining sleeve through the lumen of the second sleeve before coupling the retaining sleeve to the receiver head of the bone screw assembly. The method may further comprise moving the second sleeve between a distal position, in which the second sleeve is locked against rotation relative to the receiver head of the bone screw assembly, and a proximal position, in which the second sleeve can rotate relative to the receiver head of the bone screw assembly.

In certain embodiments, the method can further include coupling the retaining sleeve to the receiver head, inserting the driver through the lumen of the retaining sleeve, and coupling the driver adapter to the driver outside of a surgical field.

In some embodiments, the method can further include separating the driver adapter from the driver, coupling a bone cement delivery device to the driver, and delivering bone cement through the driver and the shank of the bone screw assembly.

In another aspect, a bone screw driver is disclosed that includes a distal tip and a proximal body. Further, a lumen extends from the proximal-most end of the bone screw driver to the distal-most end of the bone screw driver, and the tip is formed at a distal-most end of the bone screw driver and is configured to interface with a bone screw to impart torque thereto. Still further, the proximal body includes opposed flats formed thereon configured to allow application of torque to the bone screw driver, and the proximal body has a diameter greater than a distance between the opposed flats at a position distal to the opposed flats.

As with the various aspects and embodiments disclosed above, any of a variety of alternative or additional features can be included and are considered within the scope of the present disclosure. For example, in some embodiments, the bone screw driver can include a coupling feature formed at a location proximal to the opposed flats. The coupling feature can be configured to interface with a driver adapter in a manner that prevents axial separation of the bone screw driver and driver adapter. In certain embodiments, the coupling feature can include a groove formed around a circumference of the proximal body.

In some embodiments, the bone screw driver can include an intermediate portion extending between the distal tip and the proximal body portion, and the intermediate portion can have a diameter less than a diameter of the proximal body portion. In some embodiments, a first shoulder can be formed along the intermediate portion and a second shoulder can be formed along the intermediate portion at a position distal to the first shoulder. In certain embodiments, the second shoulder can include a tapered distal-facing surface. In some embodiments, the distal tip can have a diameter less than that of the intermediate portion.

In certain embodiments, the lumen can include at least one portion along its length with a tapering diameter. In some embodiments, a proximal-most portion of the proximal body can have a conical outer surface with a diameter that tapers toward the proximal-most end of the driver.

In another aspect, a bone screw driver adapter is disclosed that includes a distal adapter body and a proximal torque-receiving end. The distal adapter body has a diameter greater than the proximal torque-receiving end and defines a distal-facing cavity configured to receive a proximal portion of a bone screw driver. The bone screw driver adapter further includes a distal-facing surface within the cavity that includes a protrusion extending distally therefrom that is configured to be received within a lumen of the bone screw driver and impart torque thereto. The distal adapter body also includes a lock configured to engage with the proximal portion of the bone screw driver when received within the cavity to prevent axial separation of the bone screw driver and the bone screw driver adapter.

As with the aspects and embodiments disclosed above, any of a variety of alternative or additional features can be included and are considered within the scope of the present disclosure. For example, in some embodiments, the proximal torque-receiving end can include one or more flats configured to allow application of torque to the bone screw driver adapter.

In certain embodiments, the bone screw driver adapter can further include an intermediate portion extending between the distal adapter body and the proximal torque-receiving end. Further, the intermediate portion can have a diameter less than a diameter of the distal adapter body. In some embodiments, the bone screw driver adapter can include a lumen extending from a proximal-most end of the adapter to the distal-facing cavity.

In some embodiments, the lock can include one or more pivoting latches with a first end exposed along an outer surface of the distal adapter body and a second end extending into the distal-facing cavity. In some embodiments, the one or more pivoting latches can be biased to drive the second end radially inward within the distal-facing cavity.

In certain embodiments, the bone screw driver adapter can include a surgical navigation array mount disposed between the distal adapter body and the proximal torque-receiving end.

In some embodiments, the distal-facing cavity can include at least one opening formed therein that extends to an outer surface of the adapter body. In certain embodiments, the outer surface of the distal adapter body can include one or more flats formed thereon. In certain embodiments, the protrusion can include one or more flats formed thereon. In some embodiments, the protrusion can include a first portion having the one or more flats formed thereon and a second portion extending distal to the first portion and having a diameter less than a diameter of the first portion.

In another aspect, a bone screw driver is disclosed that includes a distal tip and a proximal body. Further, a lumen extends from the proximal-most end of the bone screw driver to the distal-most end of the bone screw driver. Still further, the tip is formed at a distal-most end of the bone screw driver and is configured to interface with a bone screw to impart torque thereto. The proximal-most portion of the lumen also includes one or more flat sidewall portions configured to allow application of torque to the bone screw driver.

As with the aspects and embodiments disclosed above, any of a variety of alternative or additional features can be included and are considered within the scope of the present disclosure. For example, in some embodiments, the diameter of the lumen can be greatest along the proximal-most portion having the one or more flat sidewall portions.

Any of the features or variations described herein can be applied to any particular aspect or embodiment of the present disclosure in a number of different combinations. The absence of explicit recitation of any particular combination is due solely to avoiding unnecessary length or repetition.

BRIEF DESCRIPTION OF DRAWINGS

The aspects and embodiments of the present disclosure can be more fully understood from the following detailed description taken in conjunction with the accompanying drawings, in which:

FIG. 7A is a rear perspective view of the driver adapter of the assembly shown in FIG. 1;

FIG. 7B is a front perspective view of the driver adapter of FIG. 7A;

FIG. 7C is another front perspective view of the driver adapter of FIG. 7A;

FIG. 27A is a rear perspective view of one embodiment of a bone screw driver according to the present disclosure;

FIG. 27B is a front perspective view of the driver of FIG. 27A;

FIG. 28 is a longitudinal cross-sectional view of the driver of FIG. 27A;

DETAILED DESCRIPTION

Certain exemplary embodiments will now be described to provide an overall understanding of the principles of the structure, function, manufacture, and use of the devices, systems, and methods disclosed herein. One or more examples of these embodiments are illustrated in the accompanying drawings. The devices, systems, and methods specifically described herein and illustrated in the accompanying drawings are non-limiting embodiments. The features illustrated or described in connection with one embodiment may be combined with the features of other embodiments. Such modifications and variations are intended to be included within the scope of the present disclosure. Additionally, to the extent that linear, circular, or other dimensions are used in the description of the disclosed devices and methods, such dimensions are not intended to limit the types of shapes that can be used in conjunction with such devices and methods. Equivalents to such dimensions can be determined for different geometric shapes, etc. Further, like-numbered components of the embodiments can generally have similar features. Still further, sizes and shapes of the devices, and the components thereof, can depend at least on the anatomy of the subject in which the devices will be used, the size and shape of objects with which the devices will be used, and the methods and procedures in which the devices will be used.

Bone screw inserters and related methods are disclosed herein for implanting a bone screw or portion of a bone screw assembly into bone. In some embodiments, the devices disclosed herein can include bone screw drivers configured to apply torque to a threaded shank of a bone screw assembly and implant it into bone, as well as receive a cement delivery device to introduce bone cement or other flowable material through the threaded shank. Also disclosed are driver adapters that can be coupled to a driver in order to facilitate application of torque thereto during bone screw implantation. The driver adapter can be configured to accommodate a configuration of the driver necessary for coupling with a cement delivery device and can be configured to decouple or release from the driver after implanting a bone screw shank into bone in order to allow the subsequent use of a cement delivery device in combination with the driver. The disclosed drivers and driver adapters can be reusable and can employ a number of additional components to form various assemblies, including retaining and counter-torque sleeves, driving handles, etc. Further, the devices disclosed herein can be utilized in a manner that allows setup of a bone screw inserter assembly outside a surgical field, such that a completed assembly can be passed to a surgeon or other user for immediate use in driving a bone screw assembly into bone.

Figure 1:
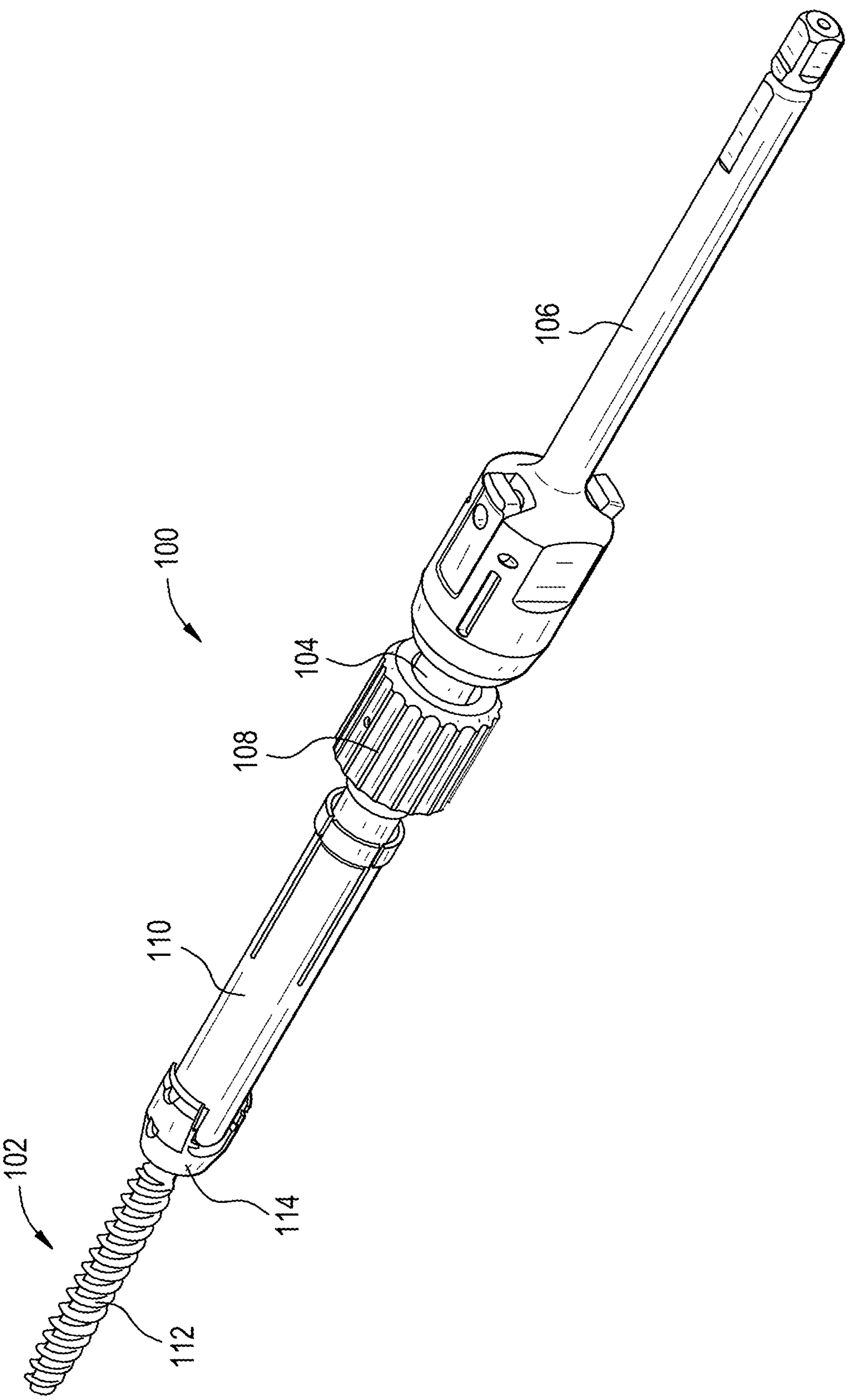
FIG. 1 is a perspective view of one embodiment of a bone screw inserter assembly according to the present disclosure coupled with one embodiment of a bone screw assembly.
Figure 2:
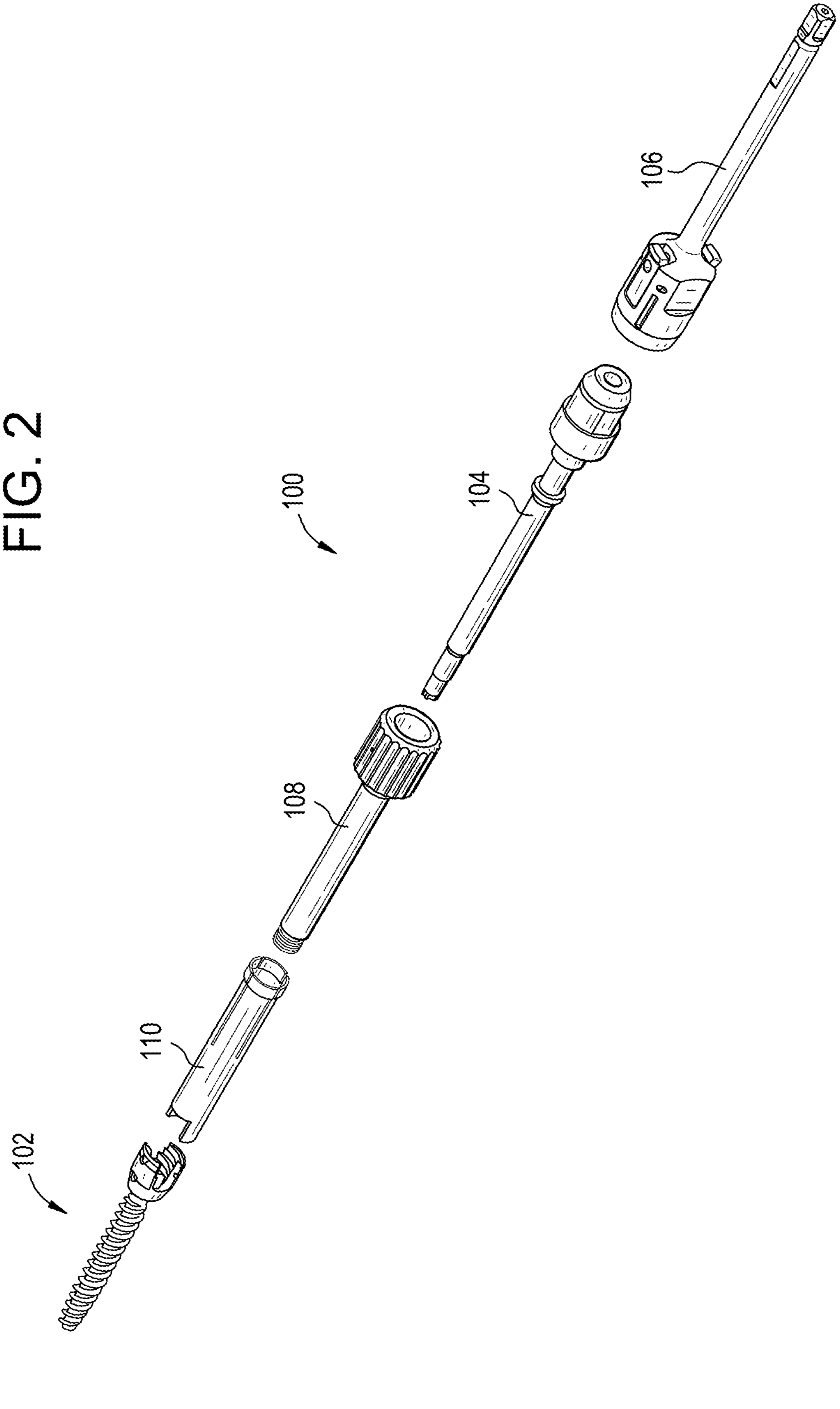
FIG. 2 is an exploded view of the bone screw inserter assembly of FIG. 1.

FIGS. 1 and 2 show one embodiment of a bone screw inserter assembly 100 according to the present disclosure coupled with one embodiment of a bone screw assembly 102. The bone screw inserter assembly 100 can include a bone screw driver 104, a driver adapter 106, a retaining sleeve 108, and a second sleeve 110. The bone screw assembly 102 can be, for example, a polyaxial bone screw having a threaded implantable shank 112 and a receiver head 114 coupled to the shank and configured for polyaxial movement relative thereto. In other embodiments, a uniplanar bone screw assembly can be utilized in which a receiver head can move in a single plane with regard to the shank. Further, in some embodiments a monoaxial bone screw can be utilized wherein a receiver head is locked against movement relative to a shank or integrally formed therewith such that no movement is possible between the receiver head and shank portions of the screw. Any of a variety of bone screws or bone screw assemblies can be utilized with the inserters disclosed herein and the illustrated bone screw assembly 102 is one example. Further details regarding various bone screws and bone screw assemblies can be found in U.S. Pat. Nos. 7,087,057; 9,155,580; 10,039,578; 10,299,839; and 10,980,574. The entire contents of each of these patents are incorporated by reference herein.

The bone screw inserter assembly 100 can be utilized to implant a bone screw assembly into bone. In the illustrated embodiment, the retaining sleeve 108 can be threadably coupled to the receiver head 114 of the bone screw assembly 102. The driver 104 can be inserted through the retaining sleeve 108 such that a distal driver tip engages with a drive feature formed on the proximal end of the threaded shank 112. A driver adapter 106 can couple with a proximal end of the driver 104 to facilitate delivery of torque thereto via, e.g., a driver handle or other instrument that can couple to the driver adapter. In addition, the second sleeve 110 can be utilized to facilitate handling and, in some embodiments, to provide counter-torque to the receiver head 114 when torqueing the threaded shank 112 to drive it into bone. As explained in greater detail below and shown in FIGS. 21 to 24B, the driver adapter 106 can be decoupled from the driver 104 and a cement delivery device can be coupled to the driver in order to deliver bone cement or other flowable material through a lumen formed in the threaded shank 112 of the bone anchor assembly 102.

Figure 3:
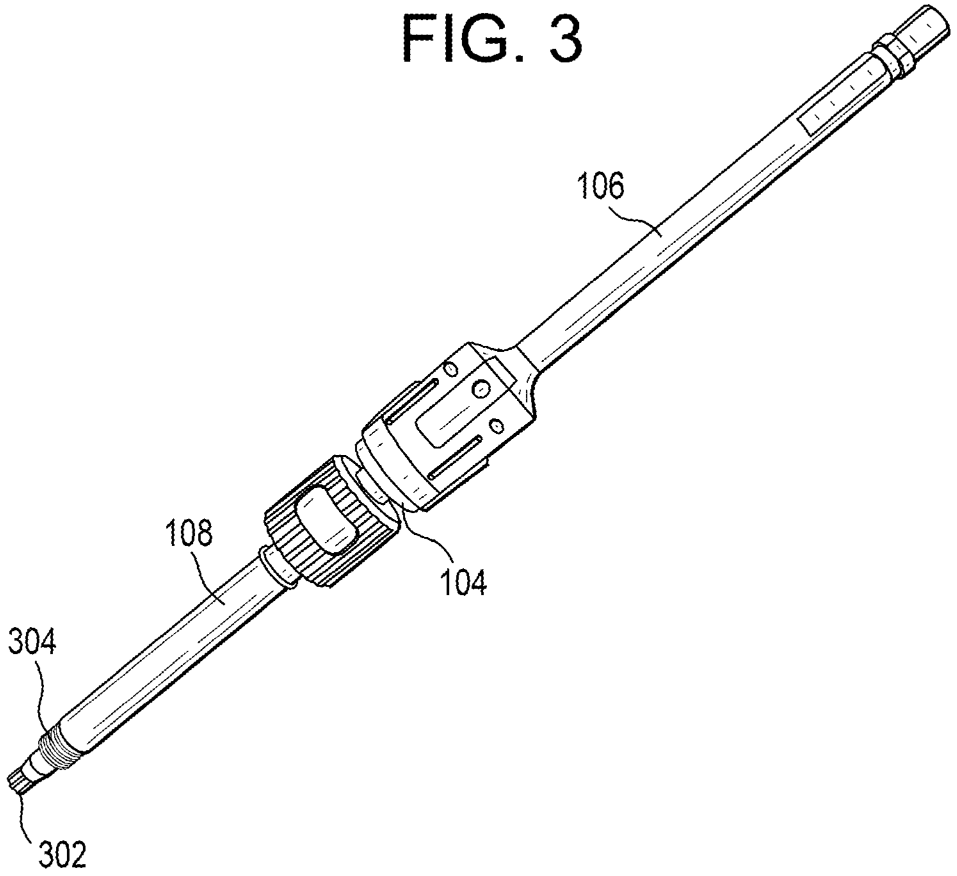
FIG. 3 is a perspective view of select components of the bone screw inserter assembly of FIG. 1.
Figure 4:
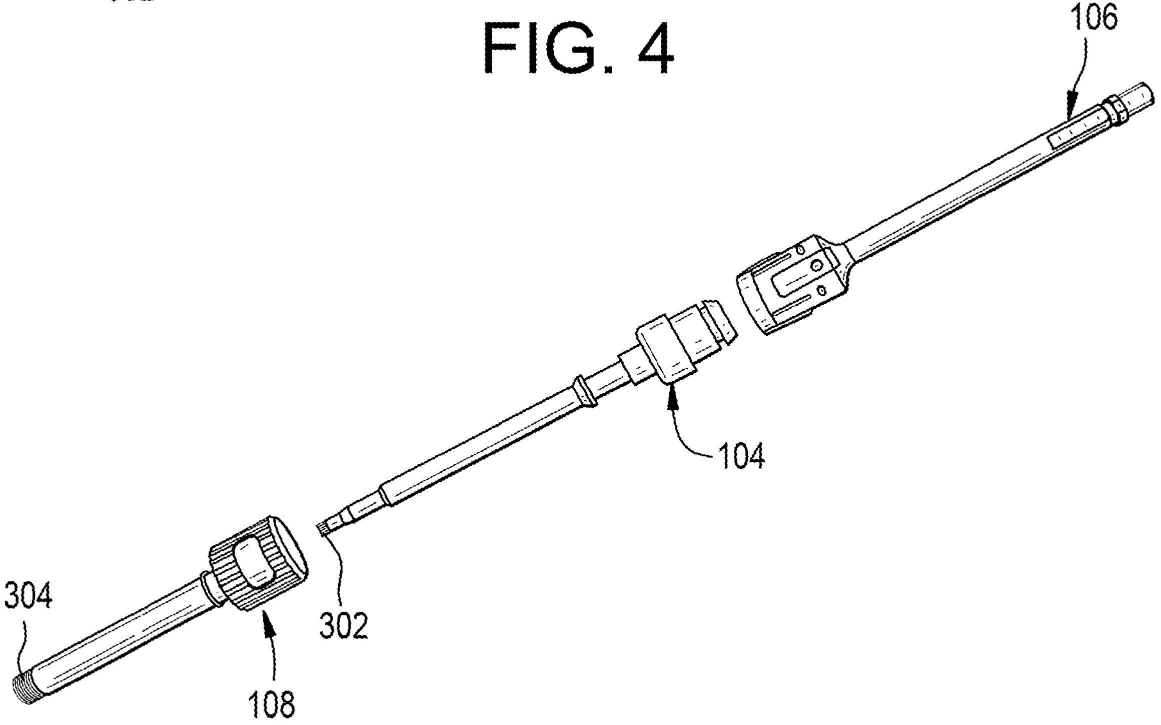
FIG. 4 is an exploded view of the select components shown in FIG. 3.

FIGS. 3 and 4 illustrate select components of the bone screw inserter assembly of FIG. 1. In particular, these figures feature the driver 104, driver adapter 106, and retaining sleeve 108. FIGS. 3 and 4 also show the drive tip 302 formed at a distal-most end of the driver 104 and the threads 304 formed at a distal end of the retaining sleeve 108. Depending on the particular application and bone screw being utilized, it can be possible to utilize an inserter assembly featuring all of the components illustrated in FIGS. 1 and 2, or a subset thereof, such as the assembly illustrated in FIGS. 3 and 4. For example, in some situations it may be possible to utilize solely a driver 104 and adapter 106, such as when driving an implantable threaded shank of a bone anchor assembly where the receiver head 114 is coupled to the shank at the surgical site after implantation.

Figure 5A:
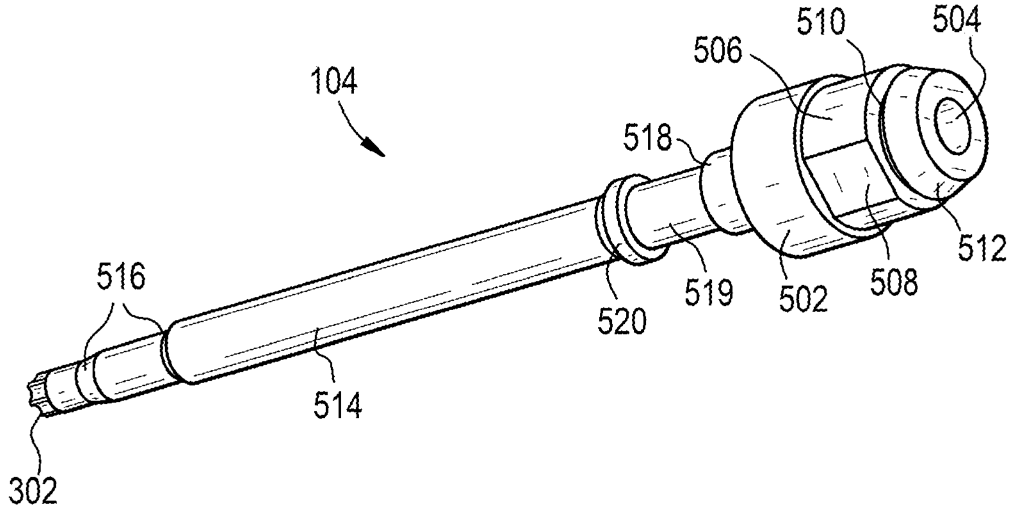
FIG. 5A is a rear perspective view of the bone screw driver of the assembly shown in FIG. 1.
Figure 5B:
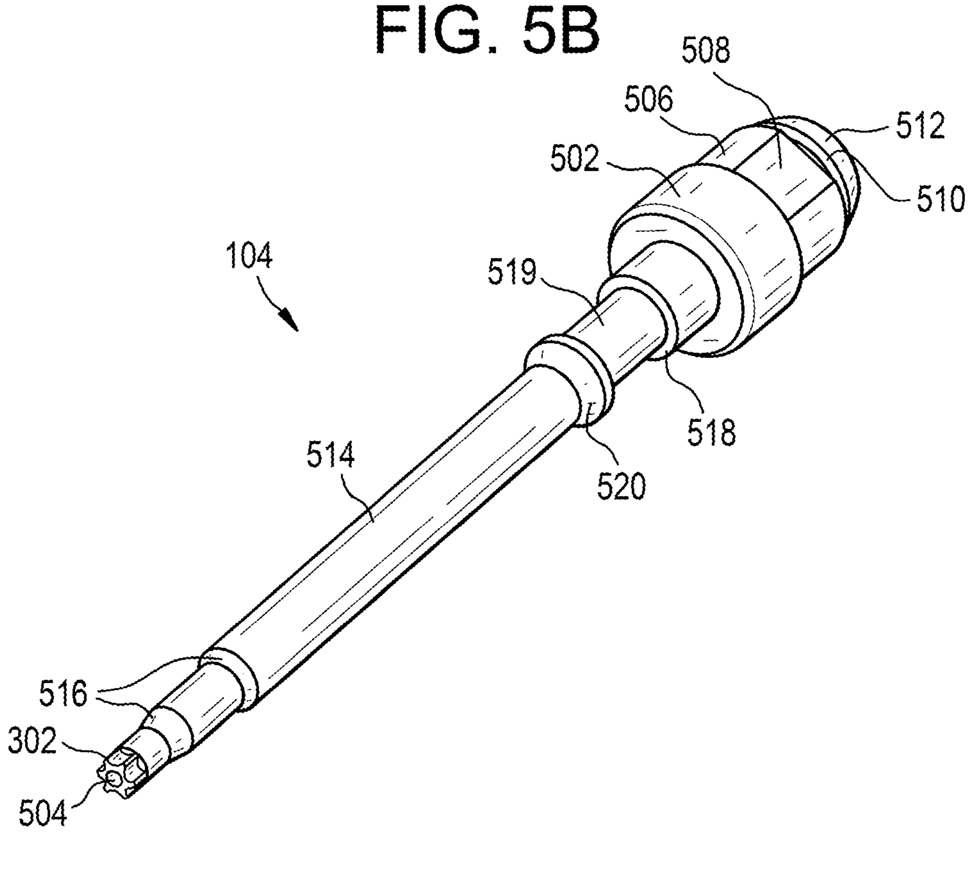
FIG. 5B is a front perspective view of the bone screw driver of FIG. 5A.
Figure 5C:
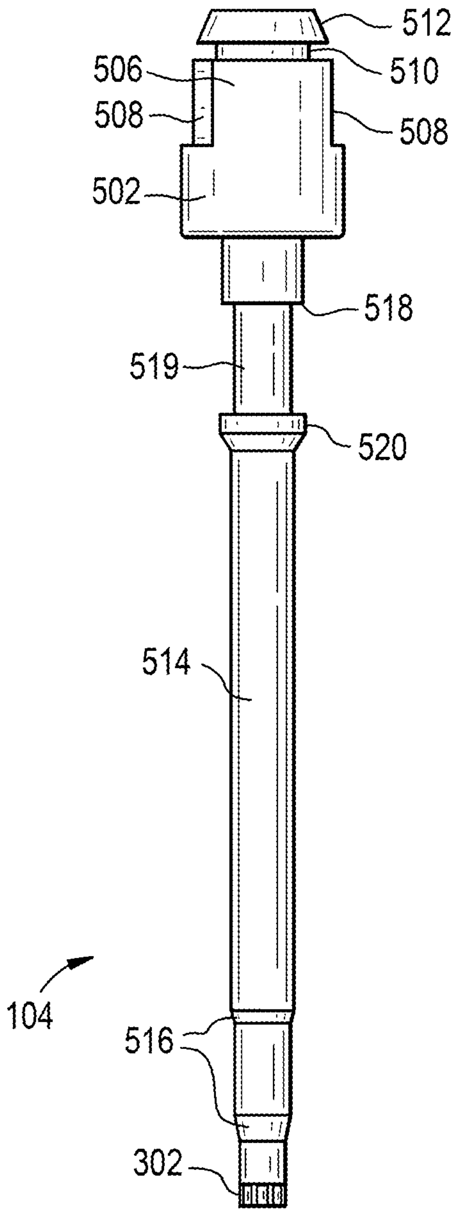
FIG. 5C is a side view of the bone screw driver of FIG. 5A.
Figure 6:
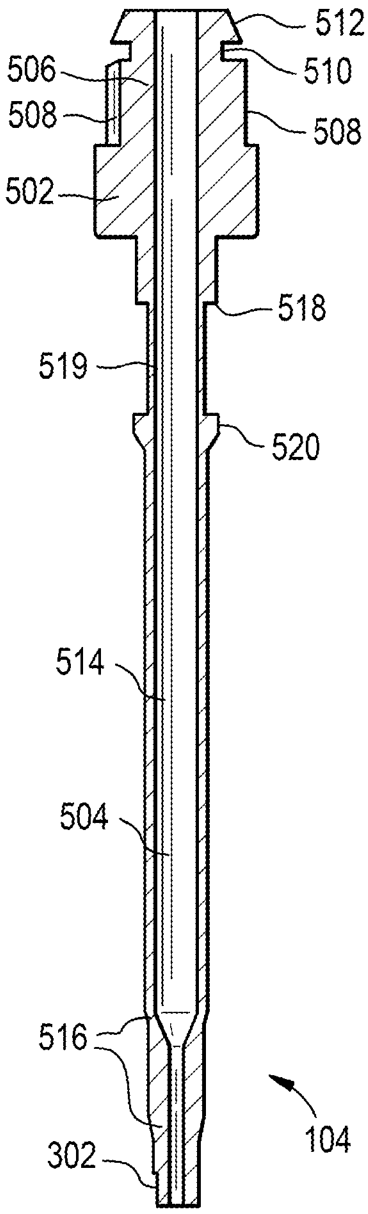
FIG. 6 is a longitudinal cross-sectional view of the bone screw driver of FIG. 5A.
Figure 8:
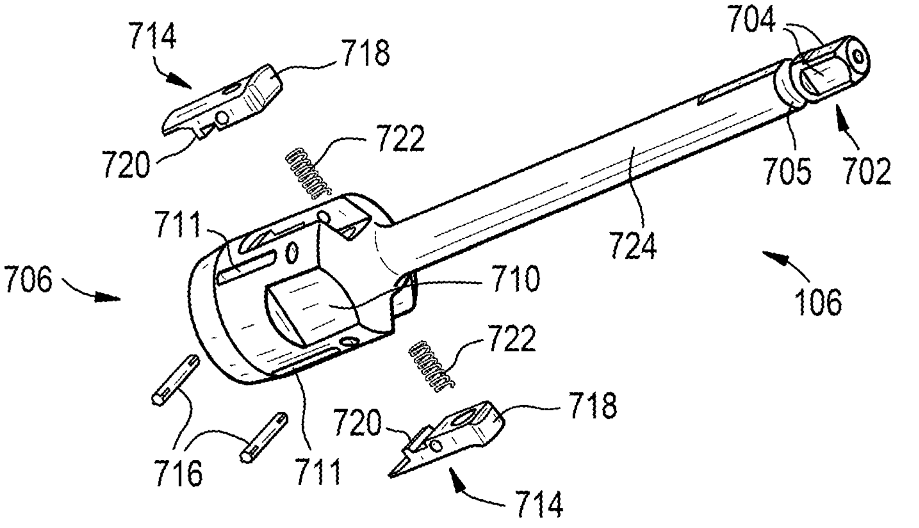
FIG. 8 is an exploded view of the driver adapter of FIG. 7A.
Figure 9:
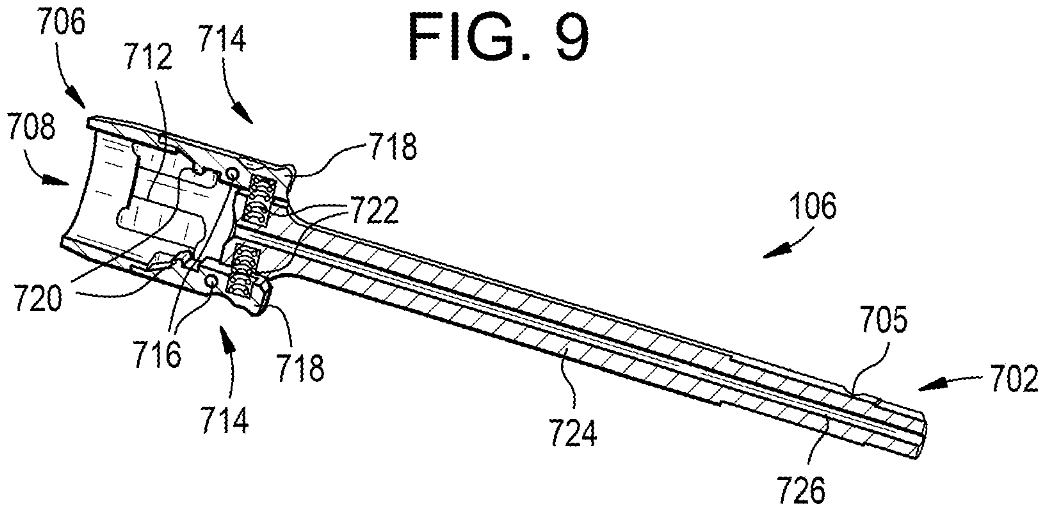
FIG. 9 is a longitudinal cross-sectional view of the driver adapter of FIG. 7A.
Figure 10:
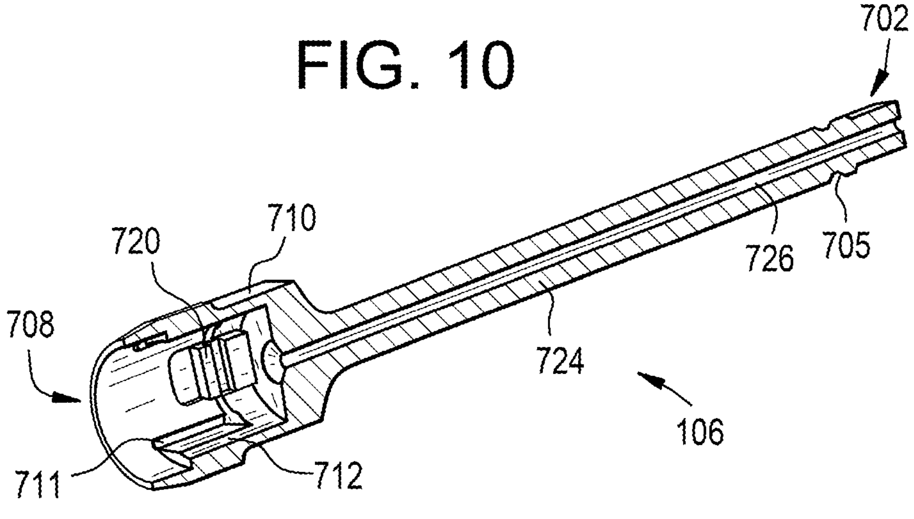
FIG. 10 is another longitudinal cross-sectional view of the driver adapter of FIG. 7A that is 90° offset from the view of FIG. 9.

FIGS. 5A to 6 illustrate the driver 104 in greater detail. While a variety of shapes and configurations are possible, in the illustrated embodiment the driver 104 includes a distal driver tip 302 and a proximal driver body 502. In addition, there is a lumen 504 extending through the driver 104 from a proximal-most end to a distal-most end thereof. The driver body 502 can have a generally cylindrical shape with varying diameters. For example, in the illustrated embodiment the driver body 502 can include a reduced diameter section 506 extending proximally that includes one or more flats 508, such as opposed flats shown in the figures, formed thereon. In some embodiments, the one or more flats 508 can extend an entire length of the driver body without being divided into different sections of varying diameter. An example embodiment of such a configuration is shown in FIGS. 32-39 and described in more detail below. As explained in more detail below, the driver adapter 106 can include a distal-facing cavity configured to receive the reduced diameter section 506 therein, as well as one or more internally-facing flats within the cavity that can interface with the one or more flats 508 and allow the driver adapter 106 to impart torque to the driver 104. In other embodiments, any of a variety of drive features can be integrated into the proximal driver body 502 to facilitate the delivery of torque thereto. For example, in some embodiments a large drive feature, such as a Torx® drive recess or other recess having one or more flat portions, can be formed in a proximal end of the driver body 502, e.g., surrounding the lumen 504. In such embodiments, a complementary drive feature can be formed on the driver adapter 106 to facilitate the delivery of torque to the driver 104 when the two components are coupled to one another. An example embodiment of such a configuration is shown in FIGS. 40-48 and described in more detail below.

The driver body 502 can further include a coupling feature to facilitate coupling and selectively securing another component relative to the driver 104. In the illustrated embodiment, the coupling feature can include a groove 510 formed around an outer circumference of the driver body 502 at a location proximal to the opposed flats. As explained in more detail below, the coupling feature can be utilized by a lock of the driver adapter 106 to secure the two components relative to one another, and similarly can be utilized by a cement delivery device to couple with the driver 104 for delivery of cement through the lumen 504 of the driver. The driver body 502 can also include a conical proximal-most portion 512 that includes a diameter that tapers toward the proximal-most end of the driver 104. This conical profile can be used to help position another component, such as the driver adapter 106 or a cement delivery device, when coupling with the driver 104. In some embodiments, the conical surface can also be utilized in conjunction with the groove 510 to facilitate securing components relative to one another.

The illustrated embodiment of a driver 104 also includes an intermediate portion 514 extending between the distal driver tip 302 and the proximal body 502. The intermediate portion 514 can have a generally cylindrical shape and can have varying diameters and lengths according to the particular application, etc. In the illustrated embodiment, for example, there can be one or more transitions or shoulders 516 formed by different diameters along a length of the intermediate portion 514. The one or more transitions or shoulders can have tapered conical surfaces or stepped surfaces that are perpendicular to one another. For example, in the illustrated embodiment a first shoulder 518 is formed along the intermediate portion 514 along with a second shoulder 520 at a position distal to the first shoulder. As explained in more detail below, the first and second shoulders 518, 520 define a length 519 of the intermediate portion 514 that can receive a lock of the retaining sleeve 108 in order to prevent unintended axial separation of the driver 104 and retaining sleeve 108 while permitting relative rotation therebetween. Further, the second shoulder 520 can include a tapered distal-facing surface and a stepped proximal-facing surface, which can facilitate the lock of the retaining sleeve 108 riding over the shoulder 520 as the driver 104 is inserted into the retaining sleeve but prevent separation without specific release of the retaining sleeve lock.

FIG. 5B illustrates the driver tip 302 in greater detail. In the illustrated embodiment, the driver tip 302 is a T27 shape configured to be received within a drive recess of complementary shape formed on a proximal end of the threaded shank 112 of a bone anchor assembly 102. In other embodiments, however, any of a variety of alternative driver tip shapes can be utilized. Also in the illustrated embodiment, the driver tip 302 has a diameter that is less than the intermediate portion 514 and the proximal body portion 502.

As noted above, the driver 104 is cannulated and includes a lumen 504 extending along its length to facilitate delivery of bone cement or other flowable material therethrough. The lumen 504 can also facilitate the delivery of the driver 104, and any bone screw assembly coupled thereto, over a guidewire. The lumen 504 have a variety of diameters based on intended application, and can also include one or more transitions 602 between different diameters along its length. As with the transitions or shoulders described above with regard to the outer surfaces of the driver 104, the transitions 602 can include conical or tapered surfaces, or stepped surfaces that form shoulders perpendicular to the sidewalls of the lumen 504. In some embodiments, the use of tapered or conical transition surfaces can help guide devices inserted through the lumen, such as an elongate tube associated with a cement delivery device, as described in more detail below and show in FIGS. 21-24B.

The driver 104 allows for delivery of a bone screw shank using, for example, the driver adapter 106 prior to delivery of bone cement or any other flowable material. As explained in more detail below, the driver adapter 106 can facilitate the attachment of a driver handle or other drive actuator to the driver 104. After removing the driver adapter 106, the cannulated driver 104 can allow the delivery of cement therethrough without requiring removal of the device or positioning of any additional components to facilitate introduction of a cement delivery device.

FIGS. 7A-10 illustrate the driver adapter 106 in greater detail. The driver adapter 106 can include a proximal end 702 configured to receive torque from a drive handle or other drive actuator. The proximal end 702 can include, for example, one or more flats 704 that can be utilized to impart torque to the driver adapter 106 and any components coupled thereto, such as the driver 104. In the illustrated embodiment, the proximal end 702 includes two pairs of opposed flats 704 forming a square drive feature, though other configurations are possible in other embodiments. The proximal end can also include a groove 705 formed around a circumference thereof. As explained in more detail below, this can be utilized in some embodiments to facilitate securing a driver handle or other drive actuator to the driver adapter 106.

The driver adapter 106 can also include a distal adapter body 706. The distal adapter body 706 can have a diameter greater than the proximal torque-receiving end 702 and can define a distal-facing cavity 708 that can be configured to receive a portion of the driver 104, such as the reduced diameter proximal portion 506 of the driver body 502. The adapter body 706 can also include one or more flats 710 formed on an outer surface thereof, which can be utilized in certain embodiments to aid in torqueing the driver adapter 106 or otherwise coupling other instrumentation thereto in a manner that prevents relative rotation therebetween. Still further, the adapter body 706 can include one or more openings 711 formed therein and extending between an outer surface of the adapter body and the distal-facing cavity 708. These openings can facilitate user visualization into the cavity 708 during coupling or release operations, as well as cleaning and sterilization of the driver adapter 106, etc.

The distal-facing cavity 708 can include interior sidewalls that feature one or more flats 712. In the illustrated embodiment, there are opposed flats 712 configured to interface with or abut against the opposed flats 508 formed on the portion of the driver 104 that can be received within the distal-facing cavity 708. The interface of the one or more flats 712, 508 on the driver adapter 106 and driver 104 can allow torque applied to the driver adapter to transfer to the driver and, in turn, torque a bone screw shank coupled to the driver by the driver tip 302.

The distal adapter body 706 of the driver adapter 106 can also include a lock configured to prevent axial separation of the driver and the driver adapter. For example, a lock can be configured to engage with a proximal portion of a bone screw driver when received within the cavity 708 to prevent removal of the driver from the cavity. Any of a variety of locks can be utilized, including locks making use of various latches, threads, grooves, magnetic or electromagnetic attraction forces, etc. The lock can include one or more pivoting latches 714, such as the opposed latches 714 shown in the illustrated embodiment. The one or more latches 714 can each be configured to pivot around a pin 716 and can each include a first end 718 exposed along an outer surface of the distal adapter body 706 and a second end 720 extending into the distal-facing cavity 708. The one or more latches 714 can each be biased to drive the second end radially inward within the distal-facing cavity in some embodiments. For example, a coil spring 722 or other biasing element can apply a force to each of the one or more latches 714 in a direction that urges the second end 720 to pivot radially inward into the cavity 708. In use, as a proximal portion of the driver 104 is received in the distal-facing cavity 708 of the driver adapter 106, the second end 720 of each of the one or more latches 714 can ride over the conical surface 512 and ultimately extend into the groove 510. This can secure the driver 104 against axial separation from the adapter 106 until a user urges the first end 718 of each of the one or more latches radially inward to free the second end from the groove.

The driver adapter 106 can also include an intermediate portion 724 extending between the proximal torque-receiving end 702 and the distal adapter body 706. The intermediate portion 724 can have a variety of lengths, shapes, and diameters. In the illustrated embodiment, the intermediate portion 724 is a generally cylindrical body having a diameter less than the diameter of the distal adapter body 706. As explained in more detail below, in some embodiments the intermediate portion can include mounting points or other features configured to facilitate coupling with other components, such as surgical navigation arrays, etc.

In some embodiments, the driver adapter 106 can include a lumen 726 extending along a length thereof. For example, the lumen 726 can extend from a proximal-most end of the driver adapter 106 to the distal-facing cavity 708. Inclusion of such a lumen can allow, for example, the use of the inserter assembly 100 in combination with a guidewire, etc.

Figure 11:
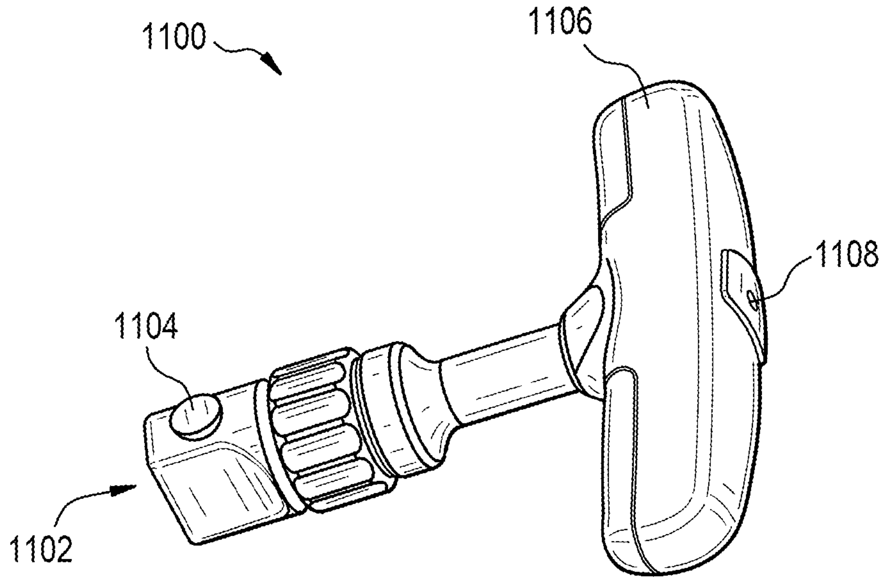
FIG. 11 is a perspective view of one embodiment of a driver handle according to the present disclosure.
Figure 12A:
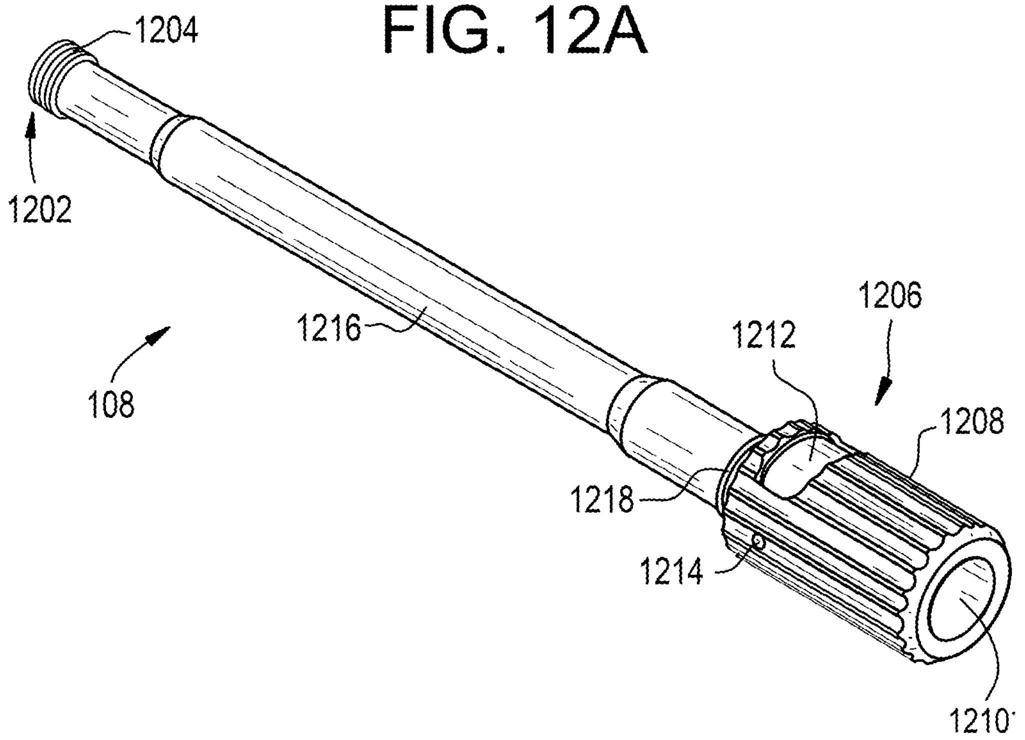
FIG. 12A is a rear perspective view of the retaining sleeve of the assembly shown in FIG. 1.
Figure 12B:
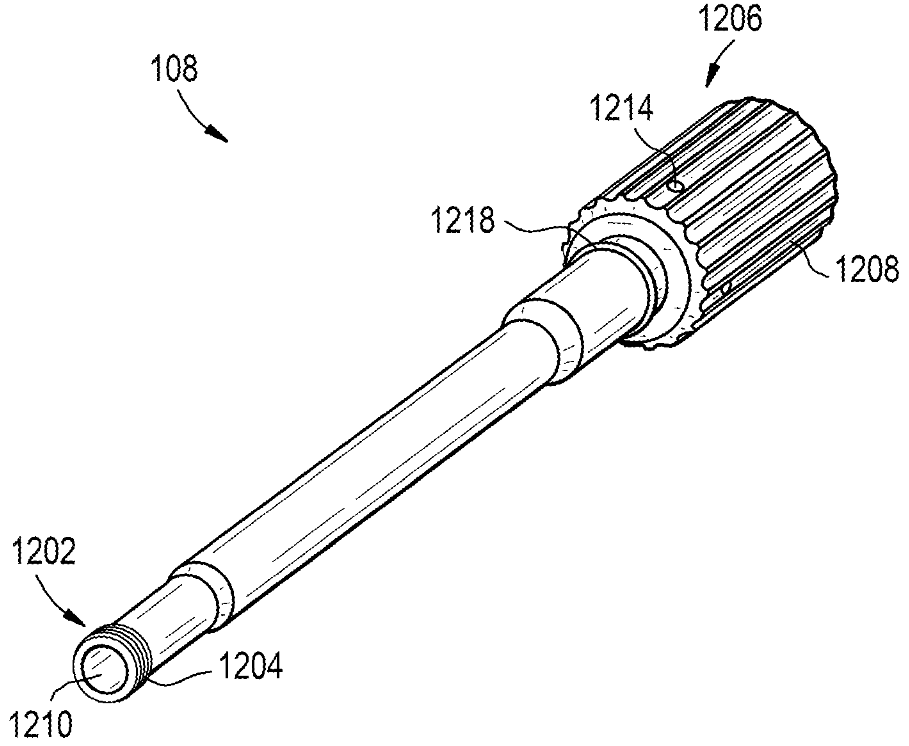
FIG. 12B is a front perspective view of the retaining sleeve of FIG. 12A.
Figure 13:
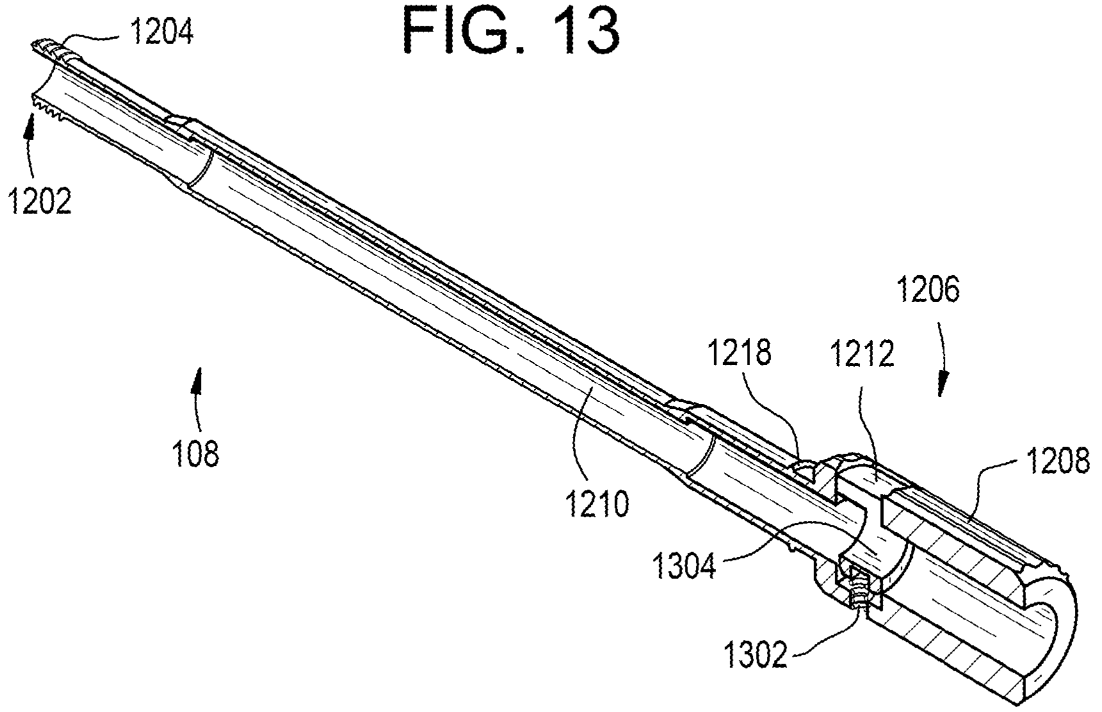
FIG. 13 is a longitudinal cross-sectional view of the retaining sleeve of FIG. 12A.
Figure 14:
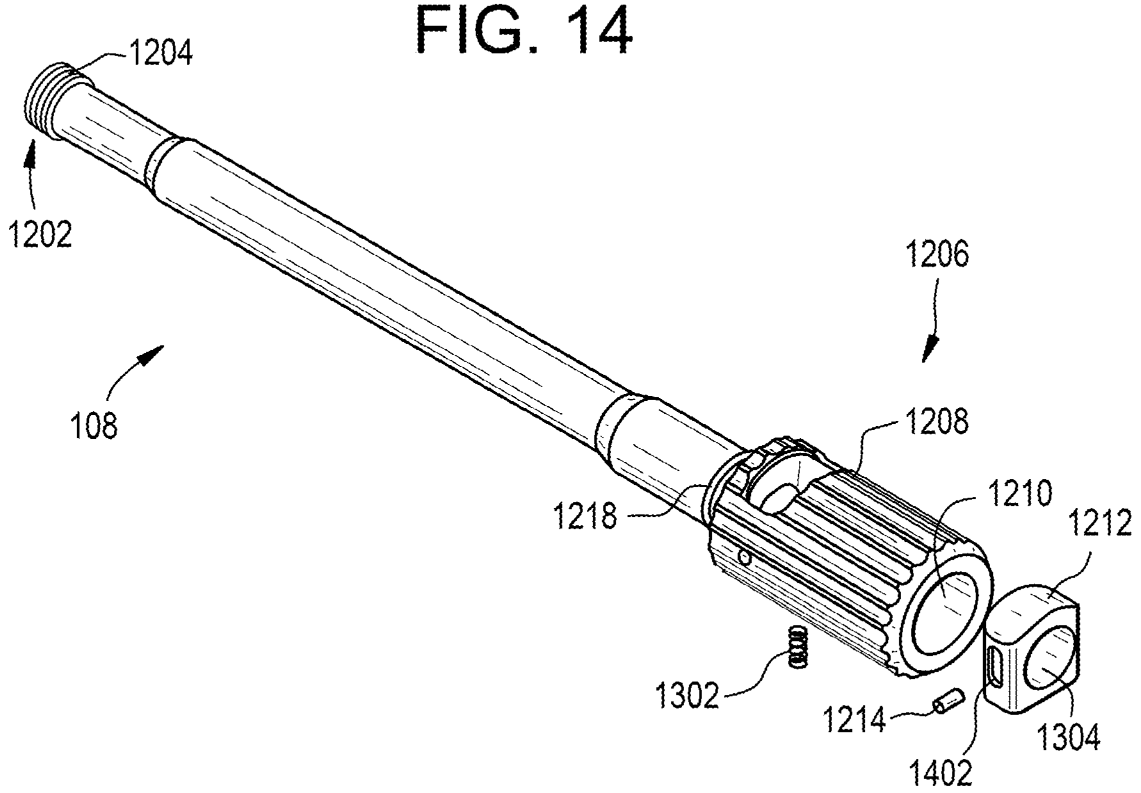
FIG. 14 is an exploded view of the retaining sleeve of FIG. 12A.

FIG. 11 illustrates one embodiment of a driver handle 1100 that can be coupled to the proximal torque-receiving end 702 of the driver adapter 106 in order to allow a user to impart torque to the driver adapter, as well as a driver 104 and bone screw shank 112 that may be coupled thereto. The driver handle 1100 can have a distal end defining a distal-facing cavity 1102 configured to receive the proximal end of the driver adapter 106. The cavity 1102 can include one or more flats complementary in shape to the one or more flats 704 formed on the driver adapter 104 in order to facilitate the transmission of torque therebetween. The driver handle 1100 can also include a lock 1104 formed along a distal portion thereof that can be utilized to secure a coupling between the driver handle and a driver adapter. For example, the lock 1104 can include a radially-translatable pin that can be urged into the groove 705 formed near the proximal end of the driver adapter 106 in order to prevent unintended separation of the components.

The driver handle 1100 can further include a user-graspable handle 1106 at a proximal end thereof to facilitate a user gripping the handle and applying torque thereto. Various shapes and sizes of handles can be utilized. In the illustrated embodiment, a T-handle shape is utilized. In addition, the driver handle 1100 can include a lumen 1108 formed from a proximal-most end thereof to the distal-facing cavity 1102. This can be utilized in connection with the lumens formed in other components described herein, to allow use of an inserter assembly 100 in connection with a guidewire, etc.

While a user-graspable handle 1100 is shown in FIG. 11, it is also possible to couple any of a variety of other driver actuators to the proximal end of the driver adapter 106 to impart torque thereto. For example, an alternative driver such as a ratchet or a powered driver such as a drill/driver can be coupled to the square drive or other drive feature formed at the proximal end of the driver adapter 106. In certain embodiments, a user-graspable handle or other driver component can be integrated into the driver adapter to create a single component with these features that cannot be separated from one another.

FIGS. 12A-14 illustrate the retaining sleeve 108 in greater detail. The retaining sleeve 108 can be a generally elongate cylindrical body and can include a distal end 1202 with threads 1204 formed thereon configured to engage with threads formed on an inner surface of a receiver head 114 of a bone screw assembly 102. The retaining sleeve 108 can also include a proximal portion 1206 having a greater diameter than the distal end 1202. The proximal portion 1206 can include a series of ridges 1208 or other surface features to facilitate a user grasping the retaining sleeve and imparting torque thereto, e.g., when coupling or decoupling the retaining sleeve with the bone screw receiver head 114.

The retaining sleeve 108 can include a lumen 1210 extending from its proximal-most end to its distal-most end to facilitate passing one or more instruments, such as the driver 104, therethrough. The retaining sleeve 108 can further include a lock configured to prevent separation of the retaining sleeve and, e.g., a driver inserted through the lumen 1210. The lock can include a button 1212 disposed within the proximal portion 1206 and capable of radial translation. A coil spring 1302 or other bias element can urge the button 1212 in one direction and a pin 1214 extending through a sidewall of the proximal portion 1206 can ride within a slot 1402 formed in the button 1212 to limit its range of motion. The button 1212 can include a through-hole 1304 formed therein that can be sized to receive the driver 104. As explained in more detail below and shown in FIG. 16, the button 1212 can ride over the shoulder 520 of the driver 104 as the driver is inserted through the lumen 1210 of the retaining sleeve 108. After passing the shoulder 520, the button 1212 can be urged by the spring 1302 in a manner that prevents separation of the driver 104 and the retaining sleeve 108 unless a user depresses the button 1212 against the biasing force of the spring 1302.

Similar to other components described herein, the retaining sleeve 108 can include an intermediate portion 1216 extending between the distal end 1202 and the proximal portion 1206. The intermediate portion 1216 can have a variety of shapes, lengths, and sizes, and can include one or more transitions of diameter or size along its length. Such transitions can feature tapered or conical surfaces for a gradual change in diameter or size, or steps that form perpendicular shoulders and instant changes in diameter or size. In addition, the intermediate portion can include one or more surface features that can be utilized to couple with additional components. For example, a ridge 1218 can be formed around a circumference of the retaining sleeve 108 at a location that facilitates desired positioning of a second sleeve that can be disposed over the retaining sleeve, as explained in more detail below.

Figure 15:
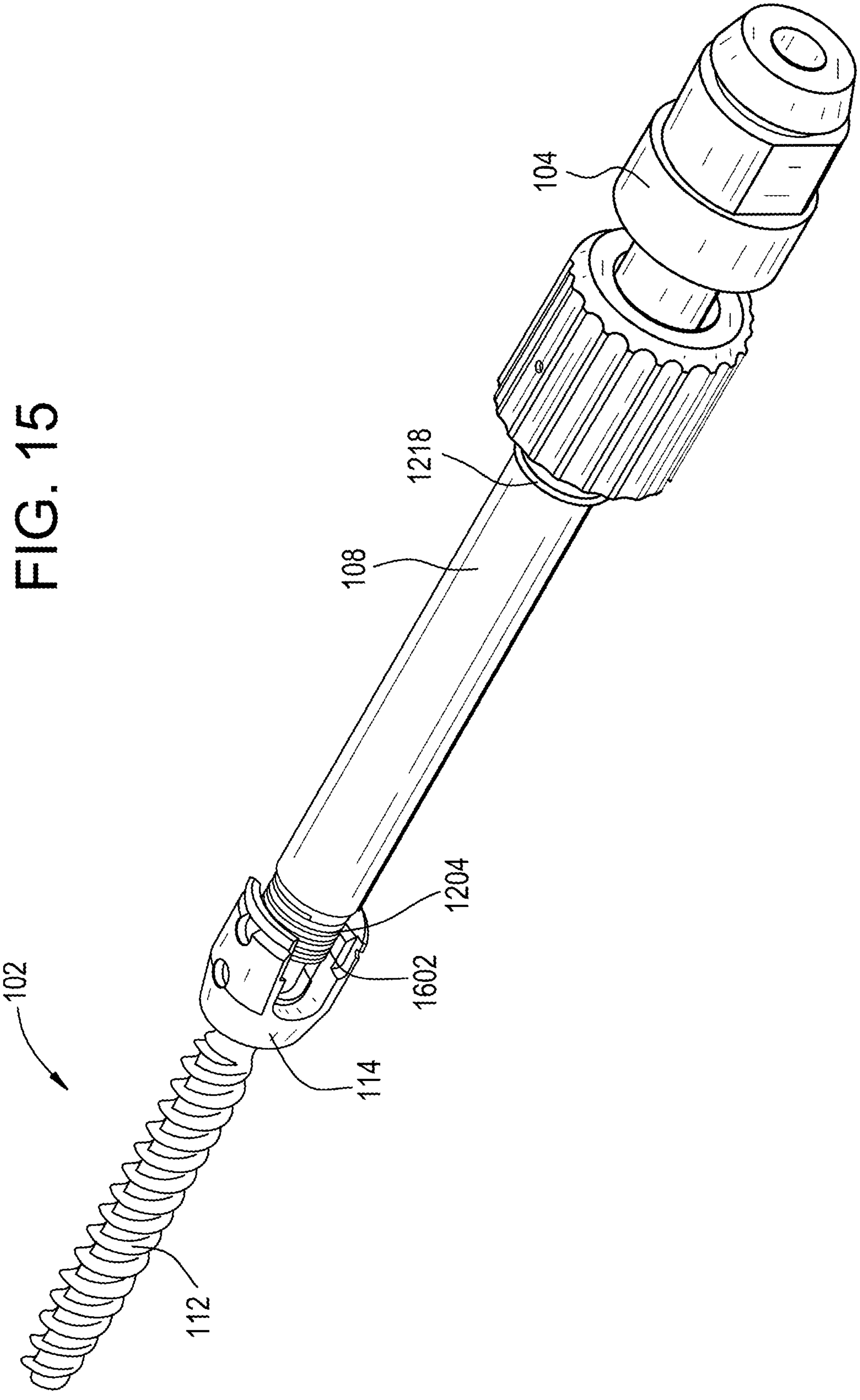
FIG. 15 is a perspective view of select components of the bone screw inserter assembly of FIG. 1.
Figure 16:
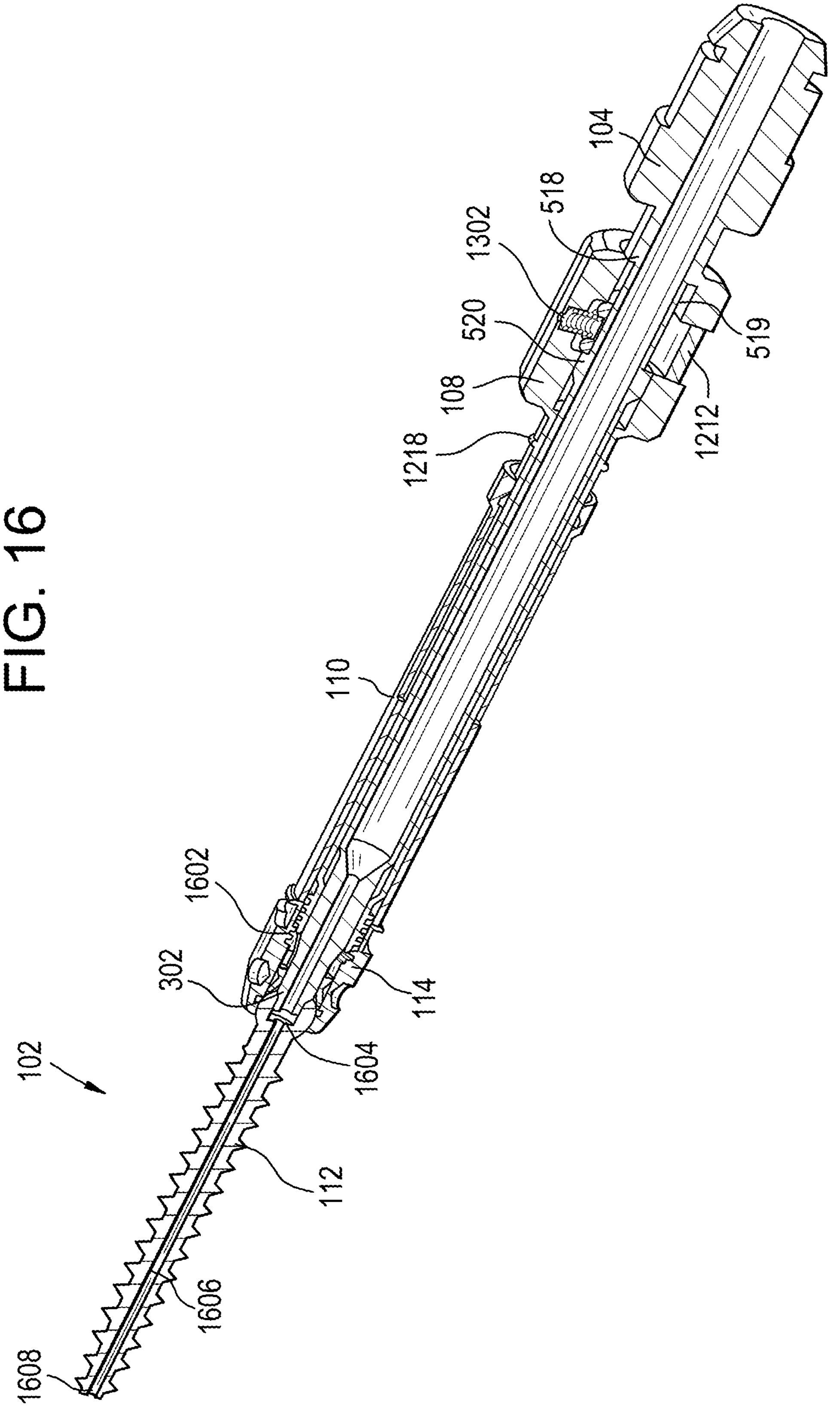
FIG. 16 is a longitudinal cross-sectional view of the select components shown in FIG. 15 and also showing the second sleeve of the assembly of FIG. 1.
Figure 17A:
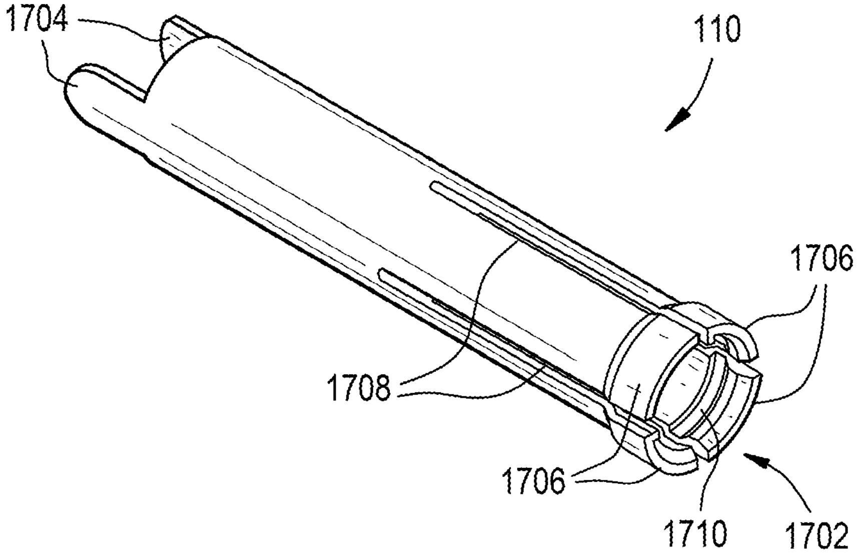
FIG. 17A is a rear perspective view of the second sleeve of the assembly shown in FIG. 1.
Figure 17B:
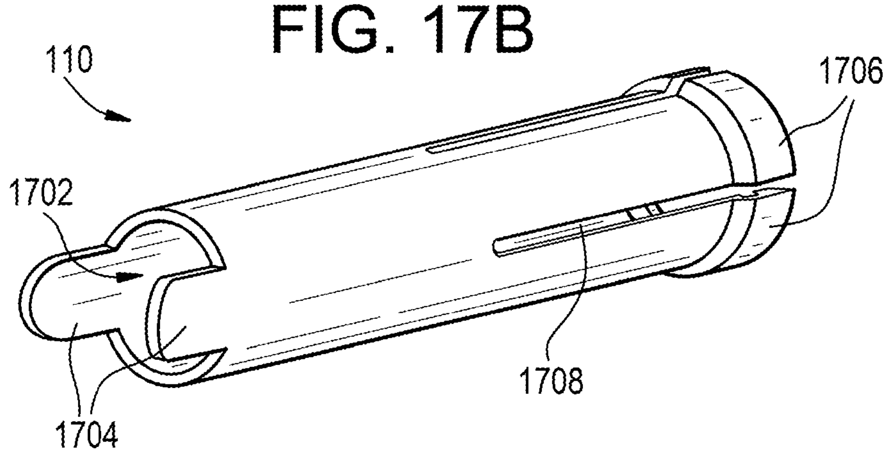
FIG. 17B is a front perspective view of the second sleeve of FIG. 17A.
Figure 18:
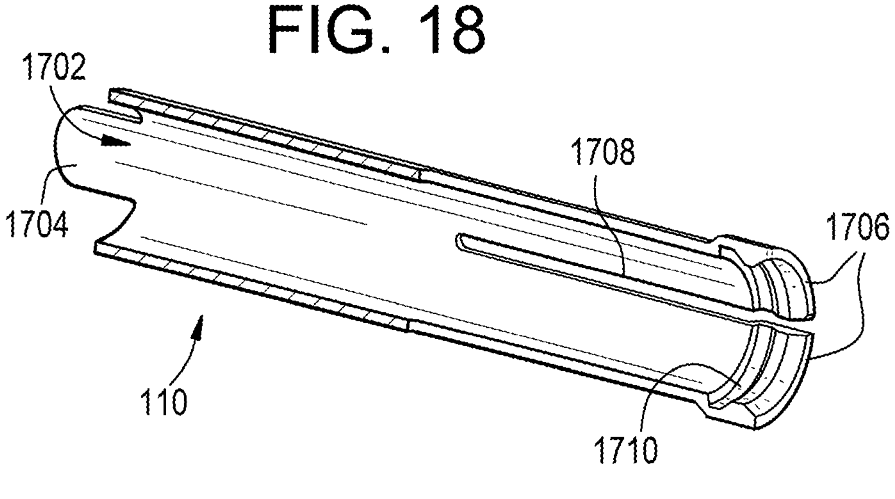
FIG. 18 is a longitudinal cross-sectional view of the second sleeve of FIG. 17A.

FIGS. 15 and 16 illustrate select components of the inserter assembly 100 of FIG. 1. FIG. 15, for example, shows the coupling of the retaining sleeve 108 to the receiver head 114 of the bone screw assembly 102, as well as the coupling of the driver 104 to the retaining sleeve and the threaded shank 112 of the bone screw assembly. FIG. 16 shows a cross-sectional view of the components shown in FIG. 15, but also illustrates the second sleeve 110 of the assembly 100. As can be seen in these figures, the retaining sleeve 108 can be coupled to the receiver head 114 of the bone anchor assembly 102 using threads 1602 formed on an internal surface of the receiver head and the threads 1204 formed at the distal end 1202 of the retaining sleeve 108. The retaining sleeve 108 can be disposed over a portion of the driver 104 such that the driver tip 302 of the driver is received within a complementary-shaped drive recess 1604 formed in the threaded shank 112 of the bone anchor assembly 102. Further, the driver 104 can be constrained relative to the retaining sleeve 108 by virtue of the lock button 1212 being positioned along the length 519 of the driver between the shoulders 518, 520. Separation of the driver 104 from the retaining sleeve 108 will be prevented until the lock button 1212 is moved against the bias force of the spring 1302 to allow the shoulder 520 to pass through the bore formed in the button.

The length 519 of the driver between the shoulders 518, 520 can be greater than the length of the lock button 1212, as in the illustrated embodiment, to facilitate some axial translation between the driver 104 and the retaining sleeve 108 when coupled. This can allow the retaining sleeve 108 to be rotated into or out of engagement with the threads of the receiver member 114 while the driver 104 remains in contact with the shank 112. Alternatively, the retaining sleeve 108 can be threaded into the receiver member 114 while the driver 104 is held proximally relative thereto (e.g., such that a proximal face of the shoulder 520 abuts the button 1212), which will slowly bring the driver tip 302 of the driver into engagement with the drive recess 1604 as the retaining sleeve is threaded further into the receiver member.

In other words, allowing some degree of axial translation between the retaining sleeve 108 and the driver 104 when coupled can allow assembly with a bone screw in either a "driver first" or "retaining sleeve first" manner, thereby providing flexibility to surgeons and other users working with the components.

Also shown in FIG. 16 is the second sleeve 110. This sleeve is illustrated in greater detail in FIGS. 17A to 20. The second sleeve 110 is a generally cylindrical body configured to be disposed over a portion of the retaining sleeve 108. The second sleeve 110 incudes a lumen 1702 extending between its proximal and distal ends. In some embodiments where the sleeve is utilized to provide counter-torque when driving a screw, the second sleeve 110 can include one or more rigid extensions 1704 or tangs formed at a distal end thereof. In the illustrated embodiment, there are two opposed rigid extensions 1704. The rigid extensions 1704 can be configured to extend into U-shaped recesses formed between opposed portions of the receiver head 114 of the bone anchor assembly 102. At a proximal end of the second sleeve 110 are one or more flexible extensions 1706 configured to deflect and ride over one or more surface features formed on the outer surface of the retaining sleeve 108. In the illustrated embodiment, the four flexible extensions 1706 are formed by four relief slots 1708 cut into the sidewall of the second sleeve 110. Further, a groove 1710 can be formed along an inner circumference of the second sleeve 110 and configured to receive a surface feature formed on an outer surface of the retaining sleeve 108, such as the ridge 1218 discussed above. In the illustrated embodiment, the groove 1710 is formed along an inner circumference of the lumen 1702 across each of the flexible extensions near a proximal end of the second sleeve 110.

Figure 19:
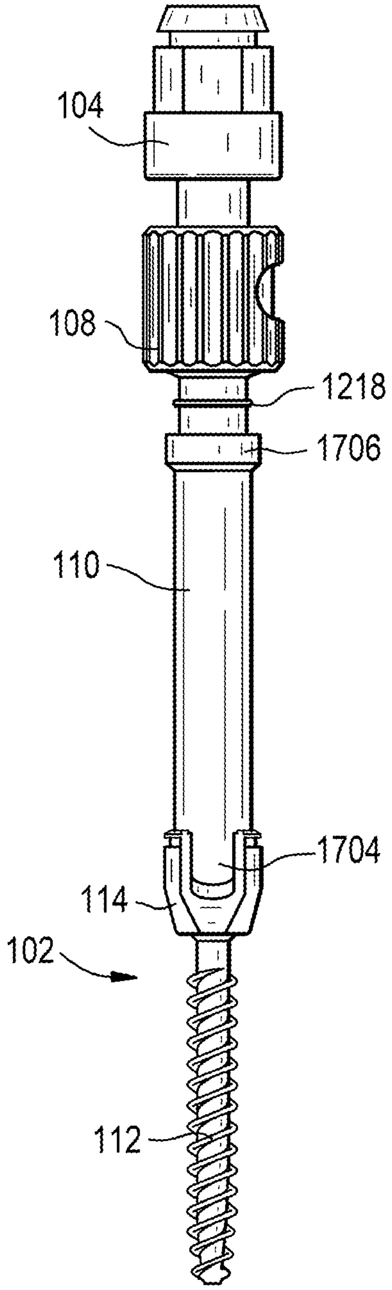
FIG. 19 is a side view of select components of the bone screw inserter assembly of FIG. 1 with the second sleeve in a distal position.
Figure 20:
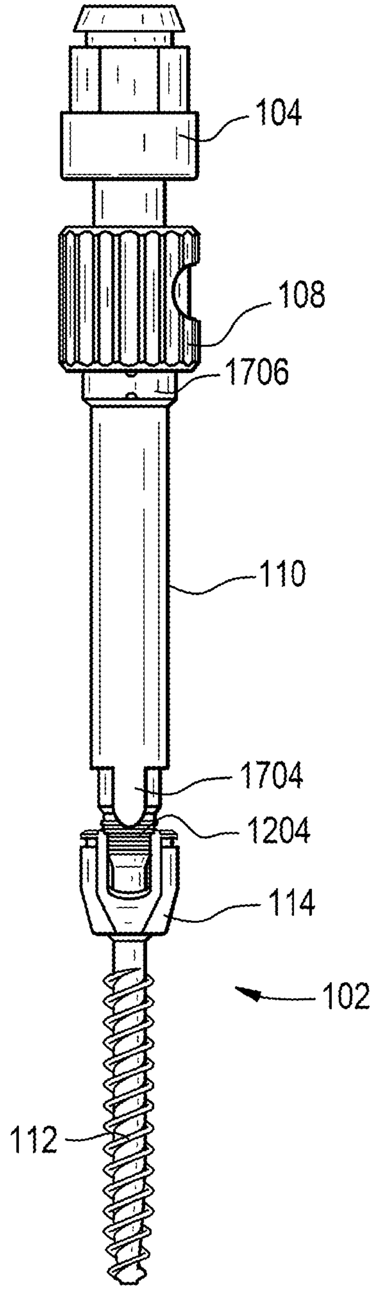
FIG. 20 is a side view of select components of the bone screw inserter assembly of FIG. 1 with the second sleeve in a proximal position.

In use, the second sleeve 110 can be disposed over a portion of the retaining sleeve 108 and can be moved between a distal position, as shown in FIG. 19, and a proximal position, as show in FIG. 20. In the distal position of FIG. 19, the rigid extensions 1704 can extend into the U-shaped recesses formed by opposed portions of the receiver member 114 or, if the rigid extensions are not present, a distal end of the sleeve 110 can abut a proximal end of the receiver member. In embodiments including the rigid extensions, disposing the sleeve 110 in the distal position can lock the sleeve against rotation relative to the receiver member due to interference between the rigid extensions 1704 and the receiver member 114. In such a configuration, a user can grasp the second sleeve 110 and use it to apply counter-torque in one direction when applying torque to the driver 104 (e.g., via a driver adapter 106 and driver handle 1100 coupled thereto) in a second direction.

When the second sleeve 110 is not in use, it can be translated proximally from the position shown in FIG. 19 to the position shown in FIG. 20. In the position shown in FIG. 20, the rigid extensions 1704 (if present) can be withdrawn proximally beyond a proximal-most end of the receiver member 114 such that they can rotate relative to the receiver member 114 without interference. In addition, in the position of FIG. 20 the groove 1710 formed on the interior surface of the flexible extensions 1706 can be disposed over the ridge 1218 such that the second sleeve 110 is retained in the proximal position until sufficient force is applied by a user to cause the flexible extensions to deflect over the ridge and advance distally. In other embodiments, the second sleeve 110 can be rotatably coupled to the retaining sleeve 108, such as by the use of threads formed on an inner surface of the sleeve that can interface with threads formed on an outer surface of the retaining sleeve.

The various components of the inserter assembly 100 described above can enable a user to setup the assembly and couple it to a bone screw assembly 102 for implantation in bone. Advantageously, such assembly can be performed outside a surgical field, such as on a "back table" or other preparation area adjacent the surgical field. This can reduce complexity of operation and the number of people operating within the surgical field. For example, in some embodiments, a user can couple a driver 104 to a retaining sleeve 108 by inserting the driver 104 through the lumen 1210 of the retaining sleeve. If a second sleeve 110 is to be utilized, it can be disposed over the retaining sleeve 108. The user can also couple the retaining sleeve 108 to a bone anchor assembly 100 by engaging the threads 1204 of the retaining sleeve with the threads 1602 of the receiver member 114. In addition, the user can couple the driver 104 to the threaded shank 112 by inserting the driver tip 302 of the driver into the drive recess 1604 of the shank 112. Further, a user can couple a driver adapter 106 to the driver 104 by inserting the proximal end of the driver into the distal-facing cavity 708 of the driver adapter until the latches 714 engage to secure the components relative to one another. A user can also couple the driver handle 1100 to the proximal end of the driver adapter 106 by, for example, inserting the proximal end of the driver adapter into the distal-facing cavity 1102 of the driver handle 1100. Coupling these components can create an assembly that is ready to pass from a preparation or staging area to a user in the surgical field who can immediately utilize the assembly to drive the shank 112 into bone. Further, if introduction of the shank 112 into bone is to be done over a guidewire, the lumens provided through the assembly 100 can enable passing the guidewire through the device and proceeding with guided delivery.

Note that a number of variations in order of coupling are possible with the assembly 100, and it is possible to utilize only select components in some embodiments. For example, a user can elect to couple the driver handle 1100 to the driver adapter 106 at any time, and also to couple these components to the driver 104. Further, the retaining sleeve 108 can be coupled to the receiver member 114 prior to insertion of the driver 104 therethrough, or the driver 104 can be coupled to the retaining sleeve 108 prior to coupling with the receiver member and/or shank 112. Similarly, the driver 104 can be inserted into the drive feature of the shank 112 prior to threadably engaging the retaining sleeve 108 to the receiver member 114, or the opposite order of coupling can be employed.

Once a shank 112 of a bone screw assembly 102 is implanted into bone, it can be desirable in some embodiments to deliver bone cement or other flowable material through a lumen 1606 formed in the shank (see FIG. 16). The bone cement or other flowable material can flow out of the shank 112 through an opening 1608 formed at a distal end thereof and/or through one or more openings formed in a sidewall of the shank (not shown). In such embodiments, a cement delivery device 2102 can be coupled to the driver 104 as shown in FIGS. 21 to 24B. The proximal portion of the driver 104 can be configured to engage with the cement delivery device 2102 using features that also facilitate coupling with the driver adapter 106, such as the groove 510 or other coupling feature and/or conical surface 512. Accordingly, to deliver bone cement or other flowable material after implanting a bone screw shank 112, a user can decouple the driver adapter 106 from the driver 104 by, for example, squeezing the first ends 718 of the pivoting latches 714 to release the second ends 720 from the groove 510 and permit proximal withdrawal of the driver adapter 106 relative to the driver 104.

Figure 21:
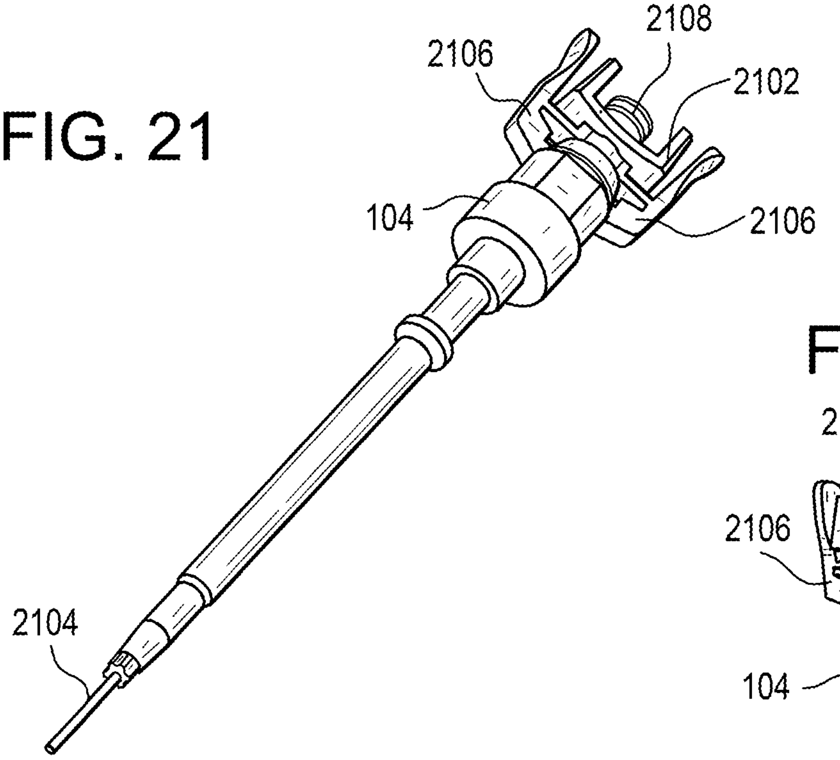
FIG. 21 is a front perspective view of the bone screw driver of the assembly shown in FIG. 1 coupled to one embodiment of a cement delivery device.
Figure 22:
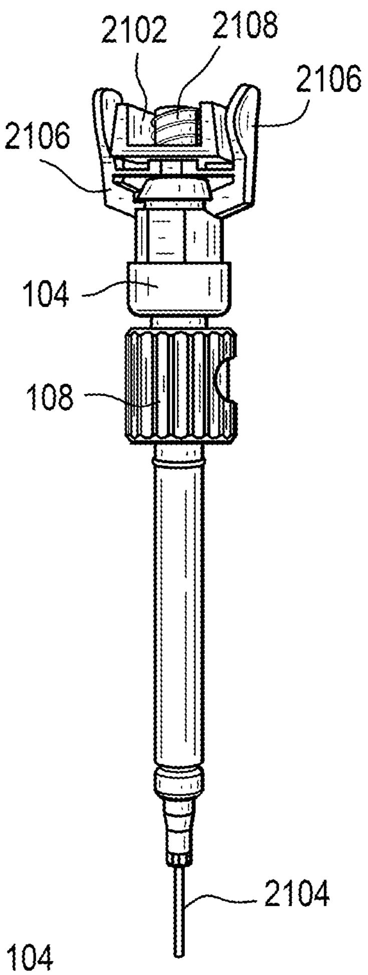
FIG. 22 is a side view of the bone screw driver and retaining sleeve of the assembly shown in FIG. 1 coupled to one embodiment of a cement delivery device.
Figure 23:
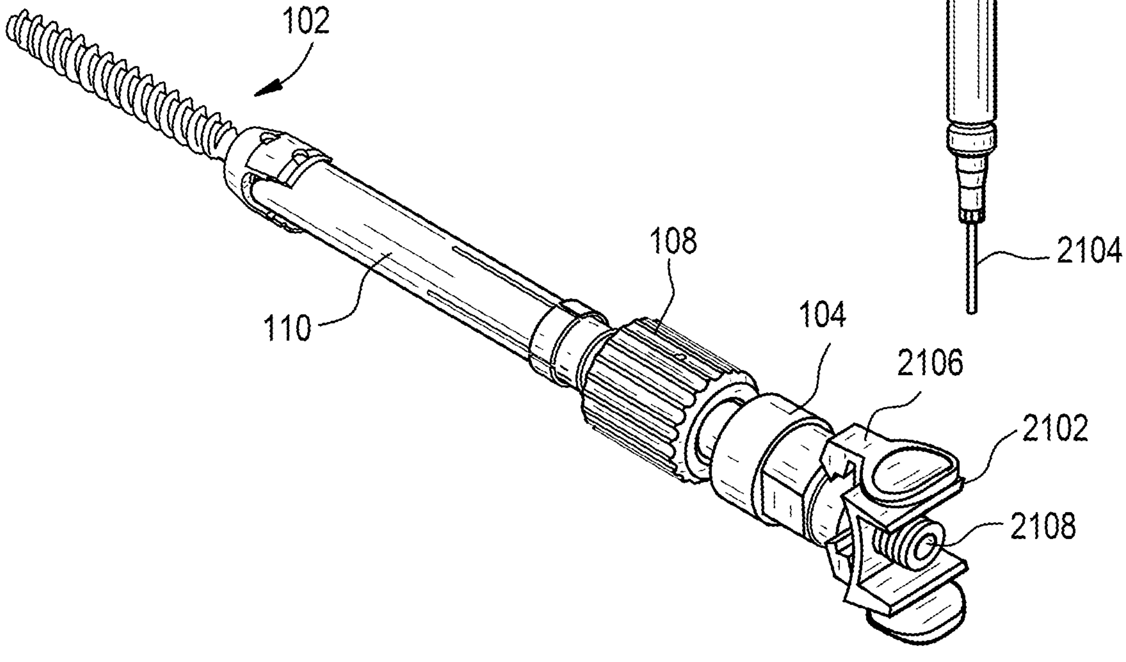
FIG. 23 is a rear perspective view of select components of the assembly shown in FIG. 1 coupled to one embodiment of a cement delivery device.
Figure 24A:
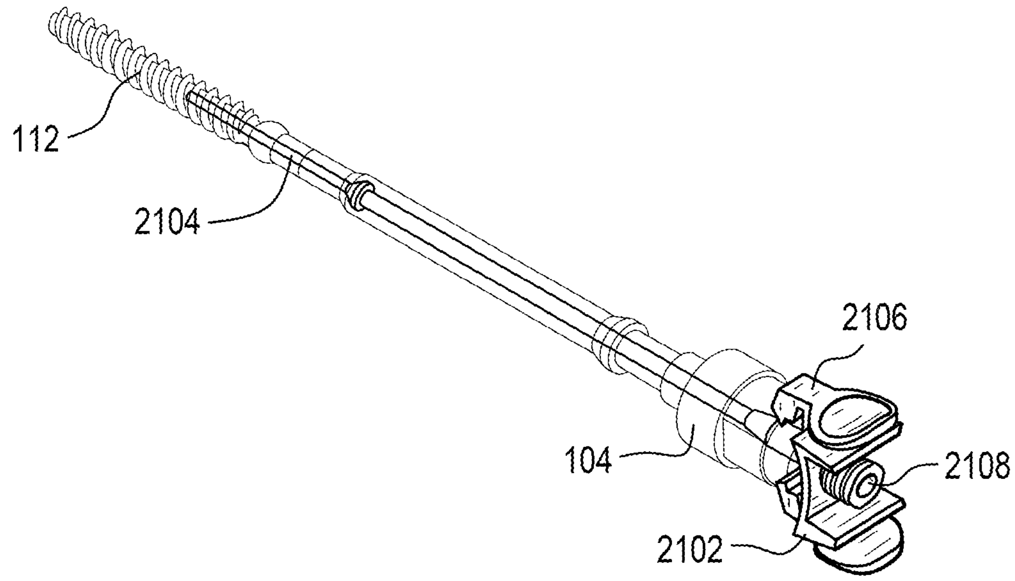
FIG. 24A is partially-transparent rear perspective view of the threaded bone anchor shank and bone screw driver of the assembly shown in FIG. 1 coupled to one embodiment of a cement delivery device.
Figure 24B:
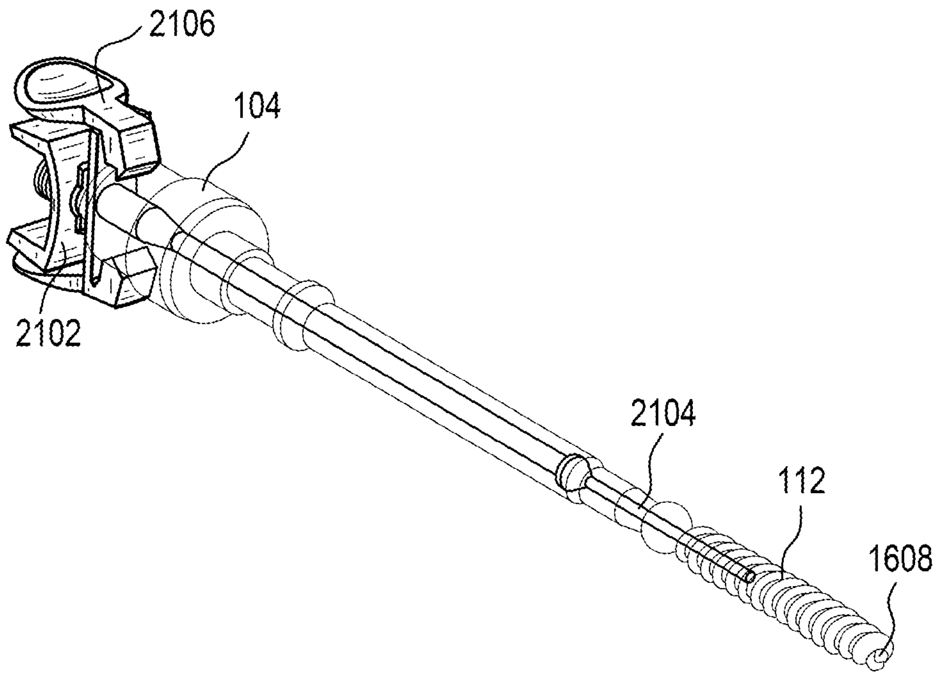
FIG. 24B is a partially-transparent front perspective view of the components shown in FIG. 24A.

With the proximal end of the driver 104 exposed, a cement delivery device 2102 can be inserted through the lumen 504 of the driver 104 such that a distal cement delivery cannula 2104 of the device 2102 extends beyond the distal end of the driver and into the lumen 1606 of the shank 112. FIG. 21 illustrates the cement delivery device 2102 and driver 104 in isolation, while FIG. 22 illustrates the cement delivery device 2102 and driver 104 in combination with the retaining sleeve 108. FIG. 23 illustrates the components of FIG. 22 in addition to the bone screw assembly 102 and the second sleeve 110. FIGS. 24A and 24B illustrate the cement delivery device, driver 104, and shank 112 in partially transparent isolation to show the positioning of the cement delivery cannula and flow path of bone cement or other flowable material.

As shown in FIGS. 21 to 24B, the cement delivery device 2102 can interface with the driver 104 with resilient clips 2106 that engage with the groove 510 formed in the driver in a manner similar to the latches 714 of the driver adapter 106. The cement delivery device 2102 also includes an inlet 2106 that can be coupled to a syringe or other device for introducing cement or other flowable material through the cement delivery cannula 2104, into the lumen 1606 of the shank 112, and out the one or more openings 1608 formed in the shank. One advantage of the devices and methods disclosed herein is that they can be configured for use with pre-existing cement delivery devices such that no changes or special adapters are needed during an operation. For example, the devices and methods disclosed herein can be compatible with cement delivery devices utilized to deliver Vertecem® and Confidence® bone cements from DePuy Synthes. Additional details regarding cement delivery devices like those that can be utilized in connection with the devices and methods disclosed herein can be found in U.S. Pat. No. 9,265,548, the entire contents of which are incorporated by reference herein.

The devices and methods disclosed herein can therefore provide a number of advantages over prior devices because a single driver can be utilized to both implant a bone screw assembly into bone and deliver bone cement or other flowable material without requiring the removal of the driver to replace with a different component. The modular driver adapters disclosed herein can allow a single driver that can interface with various cement delivery devices directly and with various torque drivers via the driver adapter. In addition, the devices disclosed herein can be reusable in nature, as they can be removed, disassembled, cleaned, and sterilized.

Figure 25:
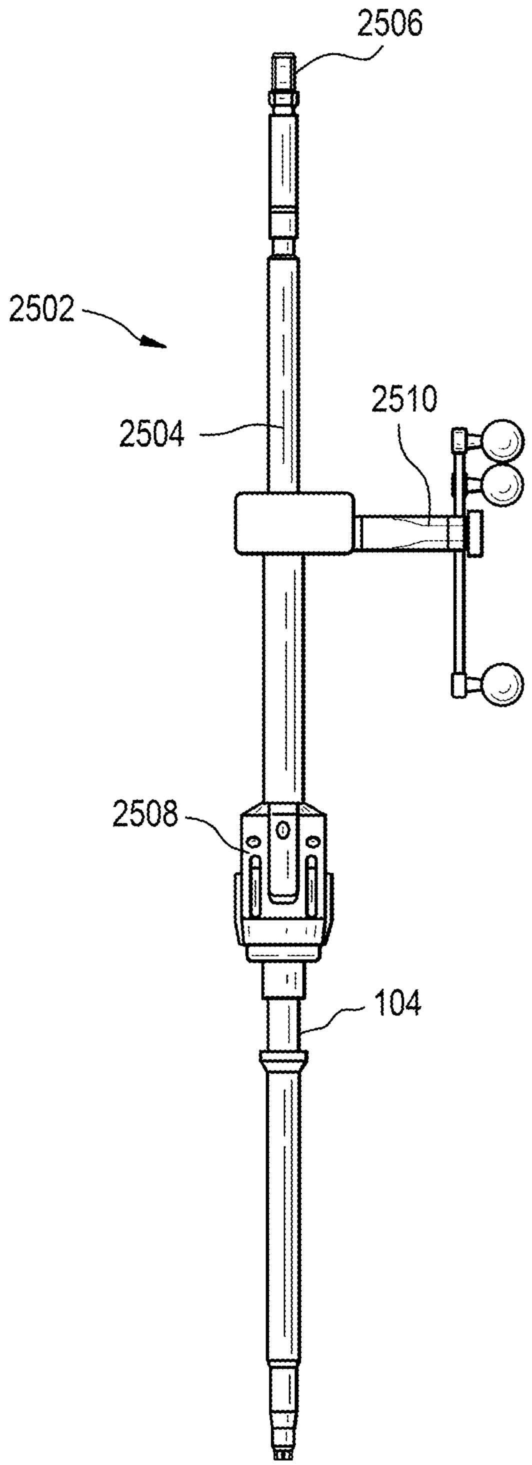
FIG. 25 is a side view of one embodiment of a navigated bone screw driver and driver adapter assembly according to the present disclosure.
Figure 26:
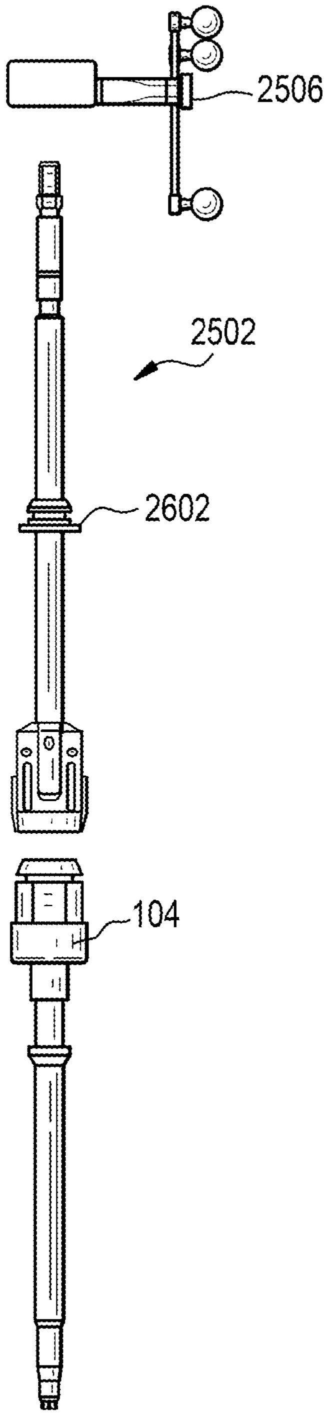
FIG. 26 is a side exploded view of the navigated bone screw driver and driver adapter of FIG. 25.

FIGS. 25 and 26 illustrate an alternative embodiment of a driver adapter 2502 that can be coupled with a driver 104. The driver adapter 2502 can operate in a similar manner to the driver adapter 106 described above. In addition, however, the driver adapter 2502 can include a surgical navigation array mount 2602 disposed along the intermediate portion 2504 between the proximal torque-receiving end 2506 and the distal adapter body 2508. The surgical navigation array mount can facilitate the coupling of a surgical navigation array 2510 to the driver adapter 2502 in a rigid manner, such that a surgical navigation system can track the three-dimensional position of the surgical navigation array in order to track the three-dimensional position of the driver adapter 2502. Providing a navigated driver adapter 2502 and coupling it to the remainder of an inserter assembly, like the assembly 100 described above, can allow surgically navigated implantation of bone screw assemblies, with all of the accompanying advantages in precision and accuracy of placement associated therewith. The surgical navigation array mount 2602 can utilize any of a variety of surgical navigation array mount configurations and can be placed at any location along the driver adapter 2502 depending on clearance requirements for other components, etc.

While the description above focuses on one embodiment of a bone screw inserter assembly 100, other embodiments are also envisioned that can include any of a variety of variations or modifications. For example, in some embodiments it can be possible to reverse the various device configurations shown and described above. In some embodiments, for example, a bone screw driver can include a cavity formed in a proximal end thereof that receives a distal portion of the driver adapter. Further, in some embodiments a proximal portion of the bone screw driver can include a lock configured to aid in coupling with a distal portion of the driver adapter and preventing axial separation of the driver and the driver adapter. Any such variations or modifications to the embodiments particularly shown and described above are considered within the scope of this disclosure.

FIGS. 27A-31 illustrate alternative embodiments of bone screw inserters that do not utilize the modular separable driver and driver adapter configuration described above. In these embodiments, a single or unitary bone screw driver can be utilized in connection with the remainder of the components described above, such as the retaining sleeve, counter-torque sleeve, and driver handle discussed in connection with the assembly 100. FIGS. 27A-28 illustrate one embodiment of a driver 2702 in detail. The driver 2702 can have a generally elongate, cylindrical shape and can include a distal driver tip 2704 and proximal torque-receiving end 2706. These components can be substantially similar to the driver tip 302 of the driver 104 and proximal torque-receiving end 702 of the driver adapter 106 discussed above. The driver 2702 can also include an intermediate portion extending between its proximal and distal ends that can have varying lengths and include one or more surface features formed thereon, including changes in diameter, ridges, shoulders, flats, etc. In the illustrated embodiment, the driver 2702 includes three shoulders 2708, 2710, 2712 formed thereon. These shoulders can define two lengths 2714, 2716 that can receive a lock of a retaining sleeve to constrain a relative position of the driver 2702 relative to the retaining sleeve, as explained in more detail below.

The driver 2702 can also include a lumen 2718 extending along its length. The lumen 2718 can facilitate use of a guidewire to insert bone screws, as well as the delivery of flowable materials in cases where the size of the lumen 2718 is acceptable and the advantages of the above-described modular and separable driver and driver adapter are not needed.

Figure 29:
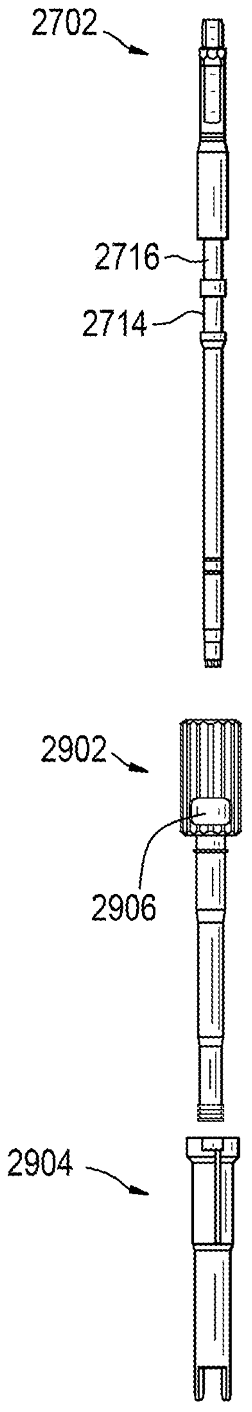
FIG. 29 is a side exploded view of one embodiment of an assembly according to the present disclosure, including a bone screw driver, retaining sleeve, and second sleeve.

FIG. 29 illustrates the driver 2702 in connection with a retaining sleeve 2902 and a second sleeve 2904. The retaining sleeve 2902 can be substantially similar to the retaining sleeve 108 discussed above, and the second sleeve 2904 can be substantially similar to the second sleeve 110 discussed above. The lengths of the driver 2702, retaining sleeve 2902, and second sleeve 2904 can be coordinated to provide desired operation. The view of this figure also highlights how the lock 2906 of the retaining sleeve 2902 can be received within either of the lengths 2714, 2716 defined by the various shoulders 2708, 2710, and 2712. In some embodiments, the sizes and positions of the lengths 2714, 2716 can be configured to allow the driver 2702 to work in connection with different types of bone screw assembly receiver heads. In particular, the lengths 2714, 2716 can be positioned to allow the driver 2702 to correctly interface with a threaded shank when the retaining sleeve 2902 is coupled to either a standard height receiver head, like the receiver head 114 discussed above, and also with a receiver head having extended reduction tabs that extend the length of the threads formed on the receiver head. More details on one embodiment of such a receiver head can be found in U.S. Pat. No. 10,463,402 (e.g., in FIG. 5A), the entire contents of which are incorporated by reference herein.

Figure 30:
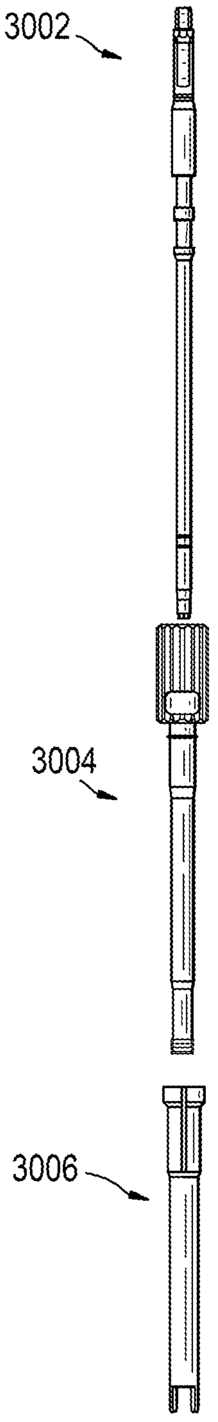
FIG. 30 is a side exploded view of another embodiment of an assembly according to the present disclosure, including a bone screw driver, retaining sleeve, and second sleeve.

FIG. 30 illustrates another embodiment of an assembly including a driver 3002, retaining sleeve 3004, and second sleeve 3006. These components can be substantially similar to those shown in FIG. 29, but can have different lengths. Any of a variety of different lengths, diameters, or other shapes can be utilized in forming the various components of a bone screw inserter assembly according the particular bone screw being inserted, area of anatomy being accessed, or other particular application parameters.

Figure 31:
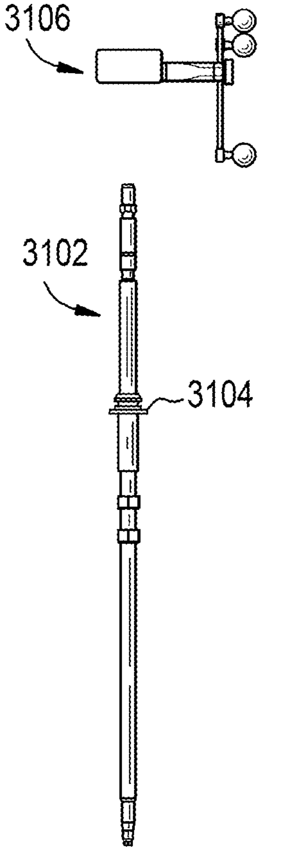
FIG. 31 is a side view of another embodiment of a bone screw driver that can be utilized in connection with the assembly of FIG. 30.
Figure 32:
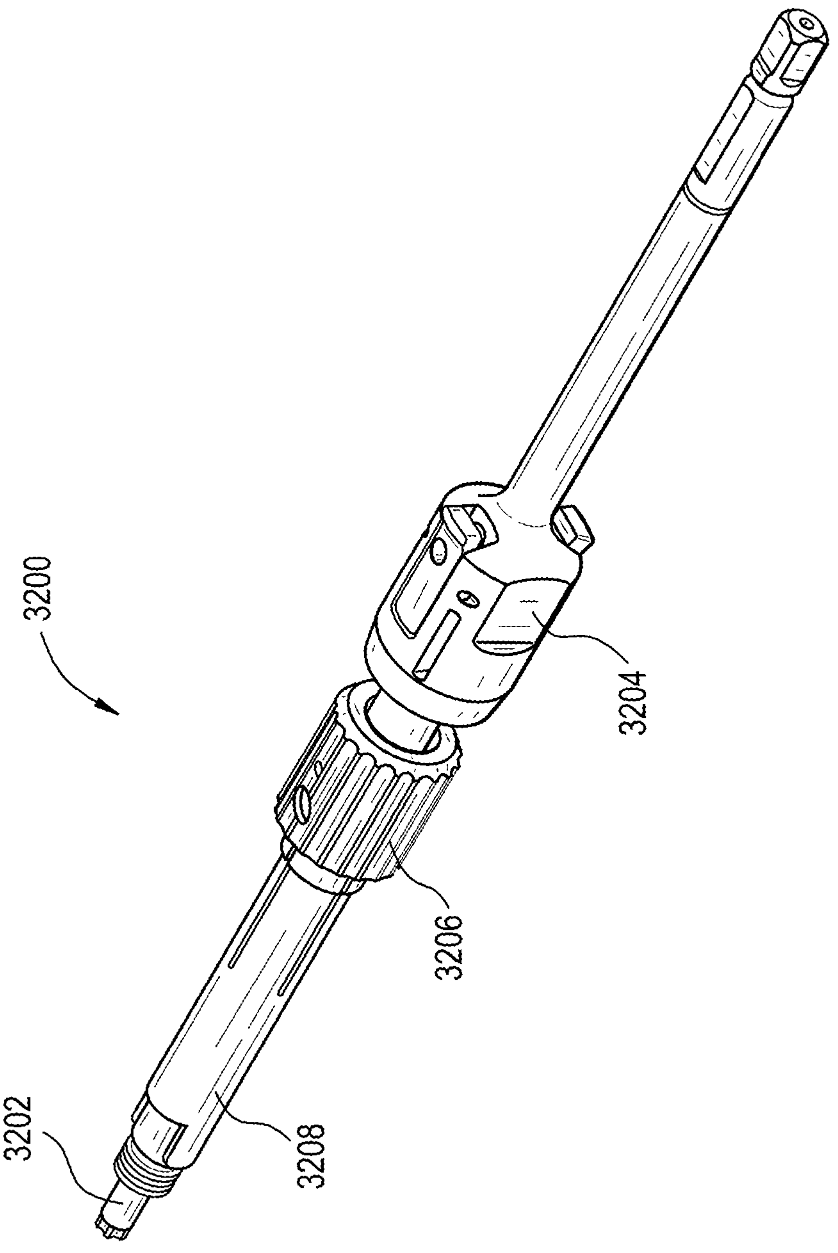
FIG. 32 is a perspective view of one embodiment of a bone screw inserter assembly according to the present disclosure.
Figure 33:
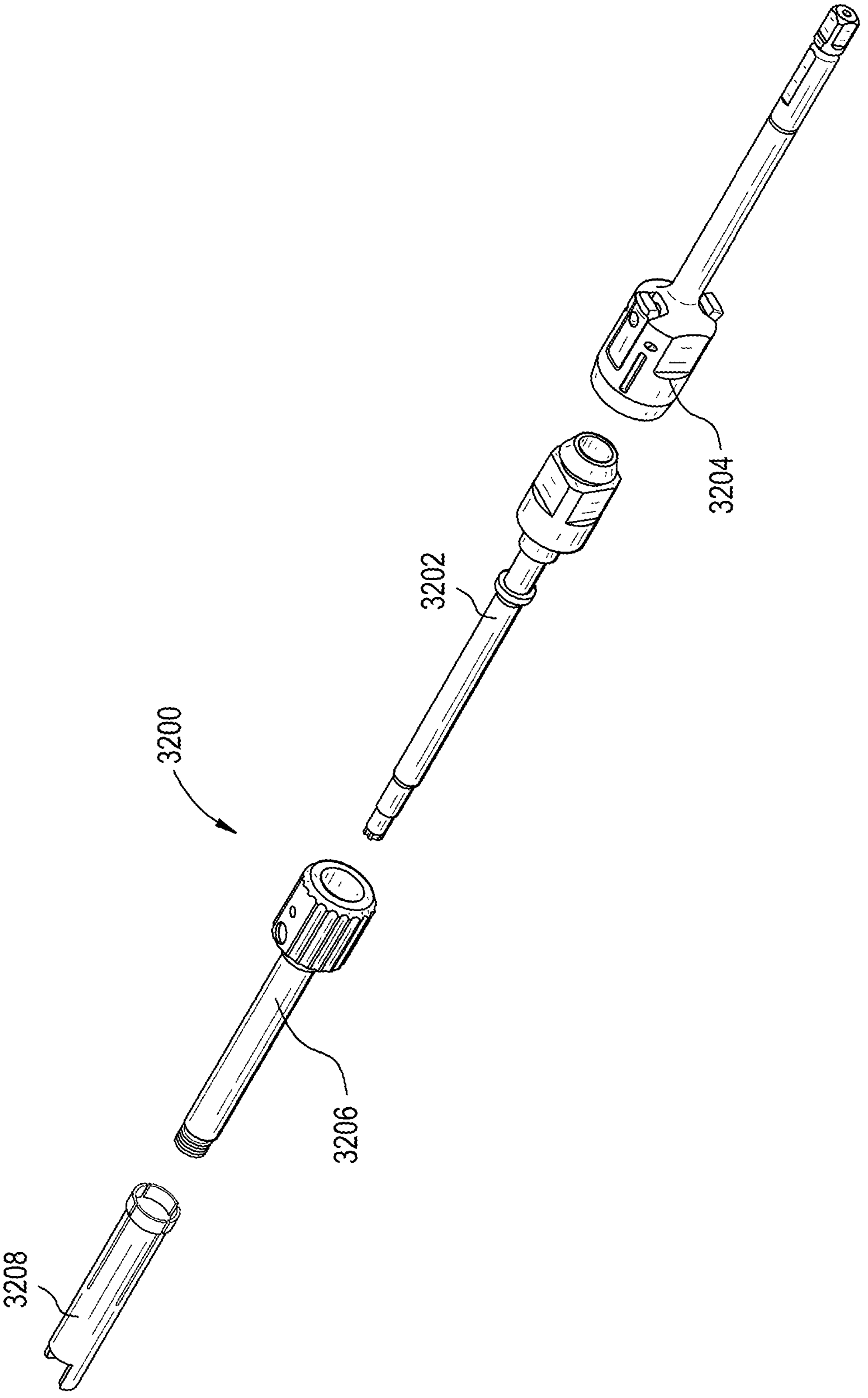
FIG. 33 is an exploded view of the bone screw inserter assembly shown in FIG. 32.

FIG. 31 illustrates still another embodiment of a driver 3102 that can be similar to either of the drivers 2702, 3002, but can further include a surgical navigation array mount 3104 disposed along a length thereof. The surgical navigation array mount 3104 can be positioned along a proximal portion of the driver 3102 such that it remains proximal to a retaining sleeve when the driver is inserted through the retaining sleeve. The surgical navigation array mount 3104 can be similar to the surgical navigation array mount 2602 discussed above and can facilitate coupling with a surgical navigation array 3106 to allow navigated insertion of bone screw assemblies.

FIGS. 32-39 illustrate another example embodiment of a bone screw inserter assembly 3200 according to the present disclosure. The assembly 3200 can be similar in many ways to the assembly 100 described above and the description below provides details regarding certain differences between these embodiments. Note that any of the various features illustrated in connection with any embodiments disclosed herein can be combined with other embodiments. The assembly 3200 includes a driver 3202, driver adapter 3204, retaining sleeve 3206, and second sleeve 3208.

Figure 34:
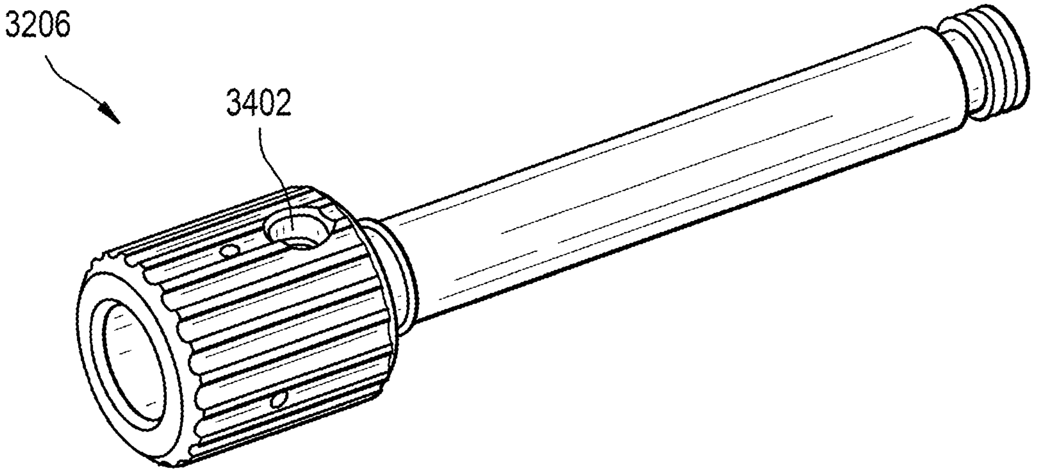
FIG. 34 is a perspective view of the retaining sleeve of the assembly shown in FIG. 32.
Figure 35:
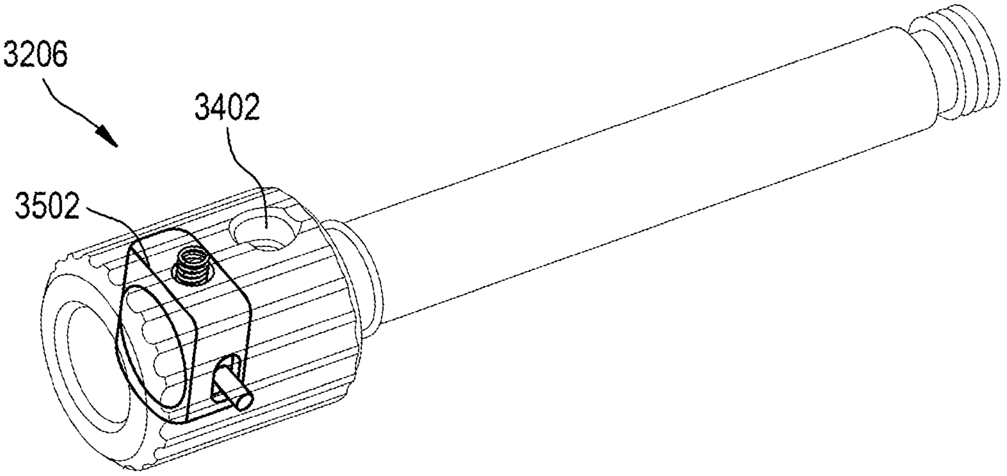
FIG. 35 is a partially-transparent perspective view of the retaining sleeve shown in FIG. 34.

FIGS. 34 and 35 illustrate the retaining sleeve 3206 in greater detail. The retaining sleeve 3206 operates similarly to the retaining sleeves described above, including the use of a lock 3502 to couple the retaining sleeve to a driver. In addition, the retaining sleeve 3206 includes one or more recesses 3402 formed along an outer sidewall thereof. The one or more recesses 3402 can receive an end of a shaft or portion of another leverage multiplying instrument to facilitate separating the retaining sleeve 3206 from a receiver member in the event removal by gripping the body directly is difficult.

Figure 36:
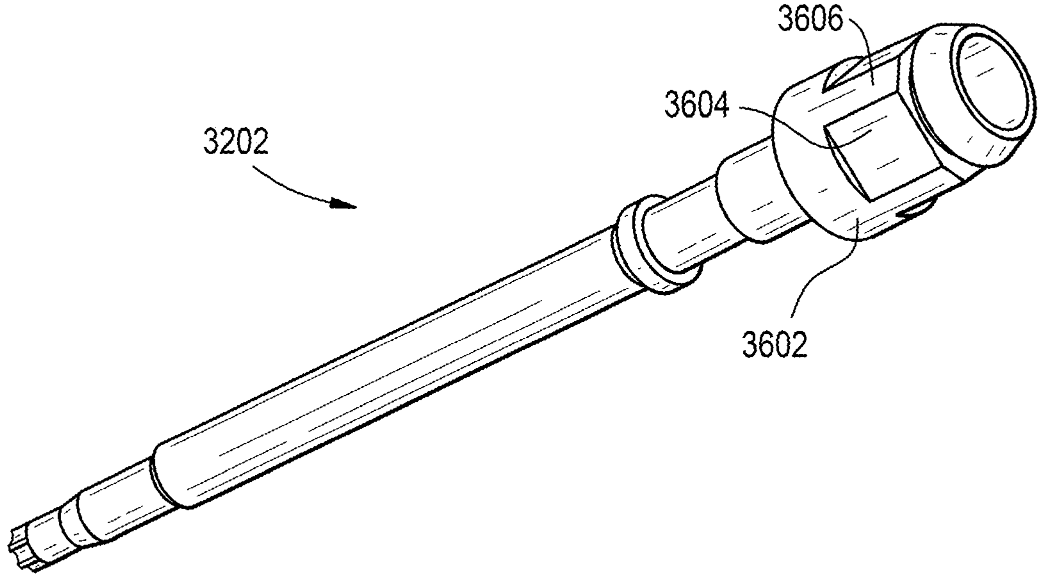
FIG. 36 is a perspective view of bone screw driver of the assembly shown in FIG. 32.
Figure 37:
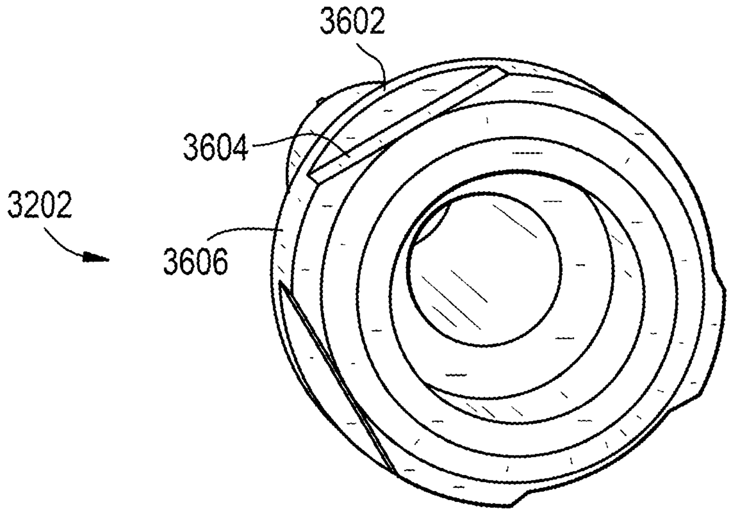
FIG. 37 is a detail rear perspective view of the bone screw driver shown in FIG. 36.

FIGS. 36 and 37 illustrate the driver 3204 in greater detail. The driver 3202 operates similarly to the drivers described above. In the illustrated embodiment, however, the driver 3202 includes a lower profile proximal body 3602 having one or more flats 3604 formed thereon. In particular, the body 3602 can have an outer surface with a constant diameter along its length that the one or more flats 3604 are formed into. This can, for example, provide an uninterrupted surface 3702 of a single diameter along the length of the proximal body 3602 along areas between adjacent edges of the one or more flats 3604. Further, while the one or more flats 3604 in the illustrated embodiment are shown extending part-way along a length of the proximal body 3602, in some embodiments the one or more flats can be formed to extend along an entire length of the proximal body.

Figure 38:
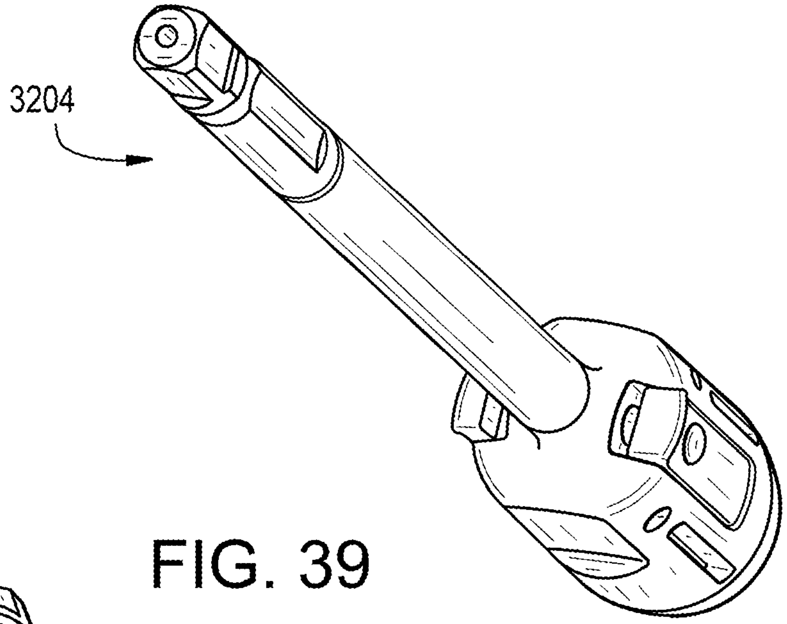
FIG. 38 is a rear perspective view of the driver adapter of the assembly shown in FIG. 32.
Figure 39:
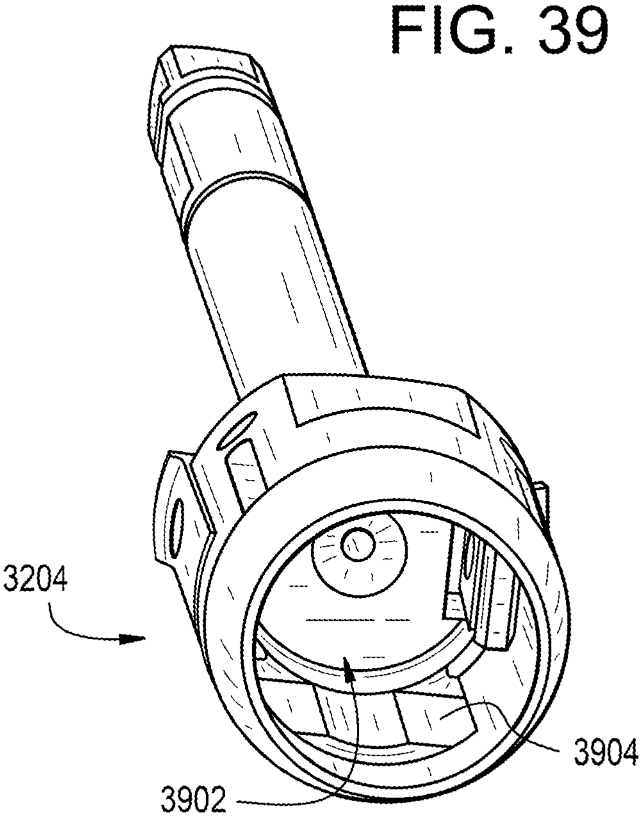
FIG. 39 is a front perspective view of the driver adapter shown in FIG. 38.

FIGS. 38 and 39 illustrate the driver adapter 3204 in greater detail. The driver adapter 3204 operates similarly to the driver adapters described above. An interior of the distal-facing cavity 3902 of the driver adapter 3204 can include one or more flats 3904 configured to interface with the one or more flats 3604 of the driver when the two components are coupled to one another.

Figure 40:
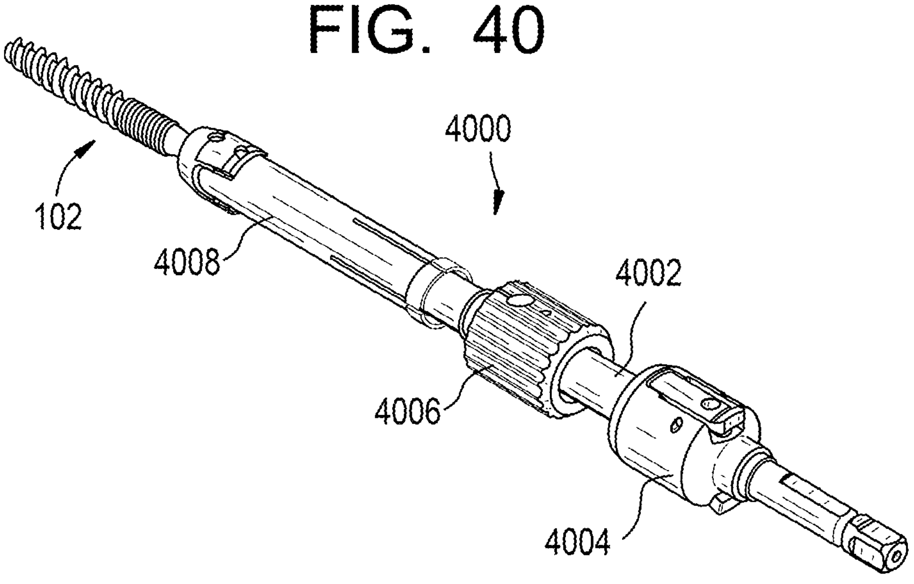
FIG. 40 is a perspective view of one embodiment of a bone screw inserter assembly according to the present disclosure.

FIGS. 40-48 illustrate another example embodiment of a bone screw inserter assembly 4000 according to the present disclosure. The assembly 4000 can be similar in many ways to the assembly 100 described above and the description below provides details regarding certain differences between these embodiments. Note that any of the various features illustrated in connection with any embodiments disclosed herein can be combined with other embodiments. The assembly 4000 includes a driver 4002, driver adapter 4004, retaining sleeve 4006, and second sleeve 4008. FIG. 40 illustrates the assembly 4000 coupled to a bone screw assembly 102 as well.

Figure 41:
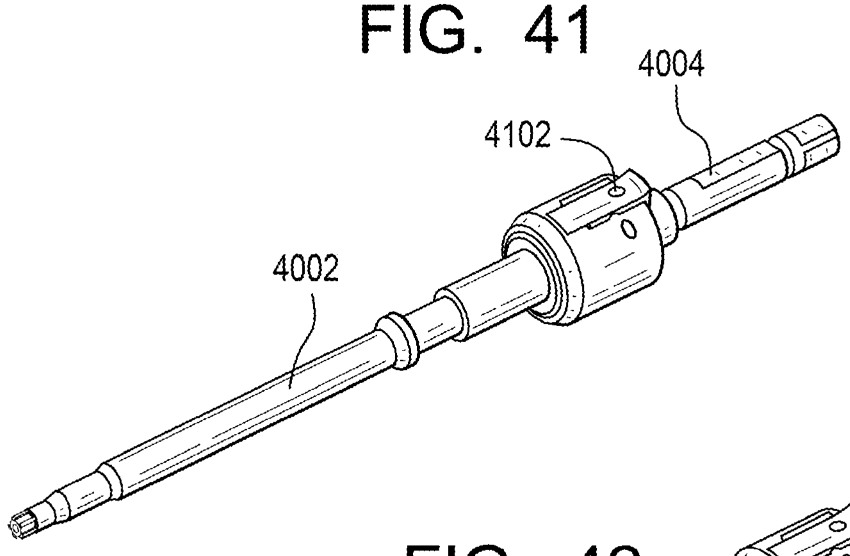
FIG. 41 is a perspective view of the bone screw driver and driver adapter shown in FIG. 40 in a coupled configuration.
Figure 42:
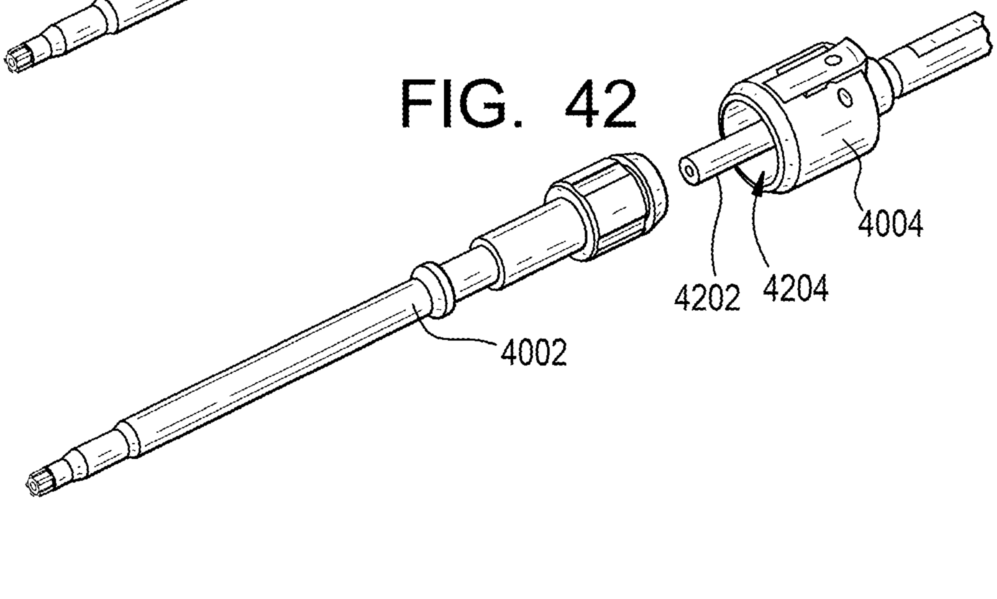
FIG. 42 is a perspective view of the bone screw driver and driver adapter shown in FIG. 41 in a separated configuration.

FIGS. 41 and 42 illustrate the driver 4002 and driver adapter 4004 in greater detail. FIG. 41 shows the two components coupled with one another such that the one or more latches 4102 lock the two components against axial separation and the driver adapter 4004 can be utilized to impart torque to the driver 4002. FIG. 42 shows the driver 4002 axially separated from the driver adapter 4004. Also visible is a protrusion 4202 extending from the distal-facing cavity 4204 of the driver adapter 4004 that can be utilized to align the two components and impart torque therebetween, as explained in more detail below.

Figure 43:
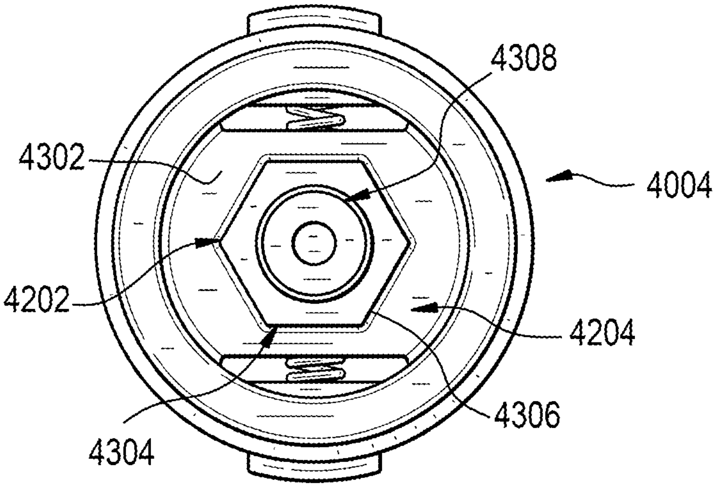
FIG. 43 is a front view of the driver adapter shown in FIG. 40.
Figure 44:
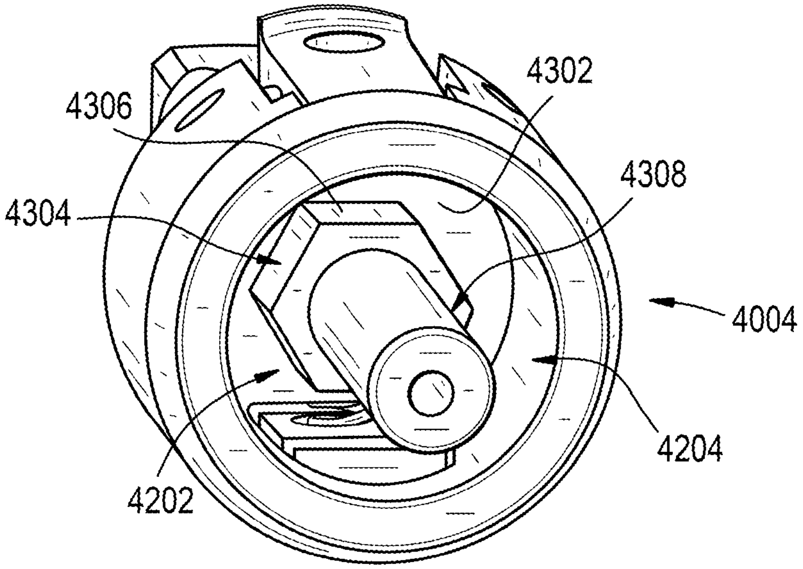
FIG. 44 is a front perspective view of the driver adapter shown in FIG. 43.
Figure 45:
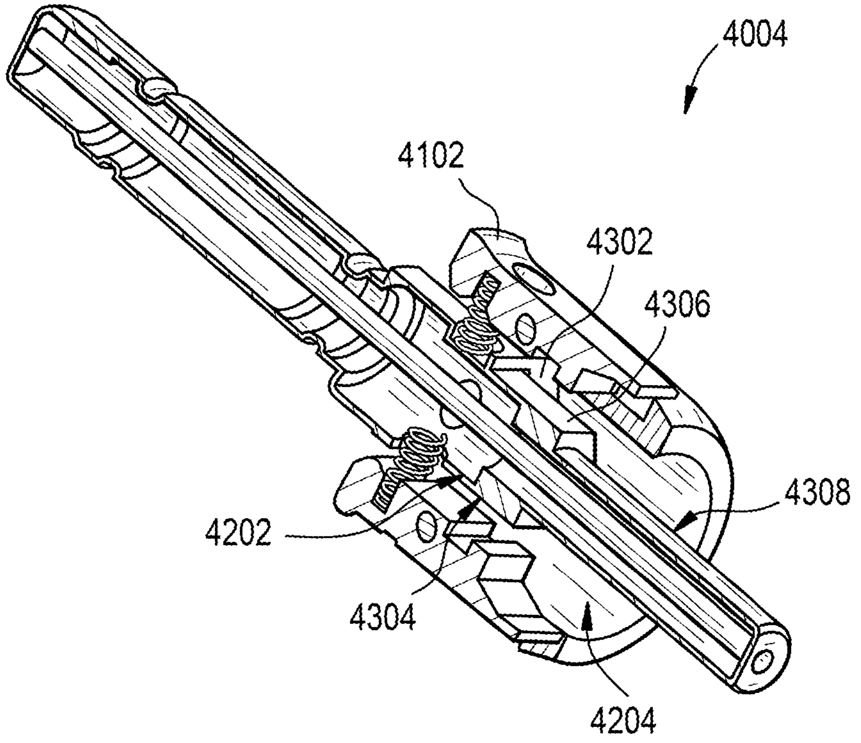
FIG. 45 is a partially-transparent longitudinal cross-sectional view of the driver adapter shown in FIG. 43.

FIGS. 43-45 illustrate the driver adapter 4004 in greater detail. The driver adapter 4004 can be similar in many ways to the driver adapters described above. As noted, however, the driver adapter 4004 can include a protrusion 4202 extending from a distal-facing surface 4302 of the distal-facing cavity 4204 of the driver adapter. The protrusion 4202 can be utilized to any of align the driver adapter 4004 with the driver 4002 and impart torque thereto. In particular, in some embodiments the protrusion 4202 can include a first portion 4304 having one or more flats 4306 formed thereon and a second portion 4308 extending distal to the first portion. In some embodiments, the second portion 4308 can have a diameter less than a diameter of the first portion 4304. The protrusion 4202 and its various portions can have any of a variety of cross-sectional shapes, e.g., in the illustrated embodiment the first portion 4303 has a hexagonal cross-sectional shape while the second portion 4308 has a cylindrical or circular cross-sectional shape. In other embodiments, however, any of a variety of shapes can be utilized for the various portions (e.g., Torx® drive shapes, curved drive shapes, keyed drive shapes, etc.). In some embodiments, a protrusion 4202 can only include one of the portions described herein. In embodiments where the protrusion includes only a profile like that of the second portion 4308, the distal-facing cavity 4202 can include one or more flats formed along other portions thereof to impart torque between the driver adapter and a driver, as described above. In embodiments where a protrusion includes features configured to impart torque to a driver, such as the first portion 4304 with one or more flats 4306, the distal-facing cavity 4204 can have a substantially cylindrical outer sidewall, as shown in FIGS. 43 and 44.

Figure 46:
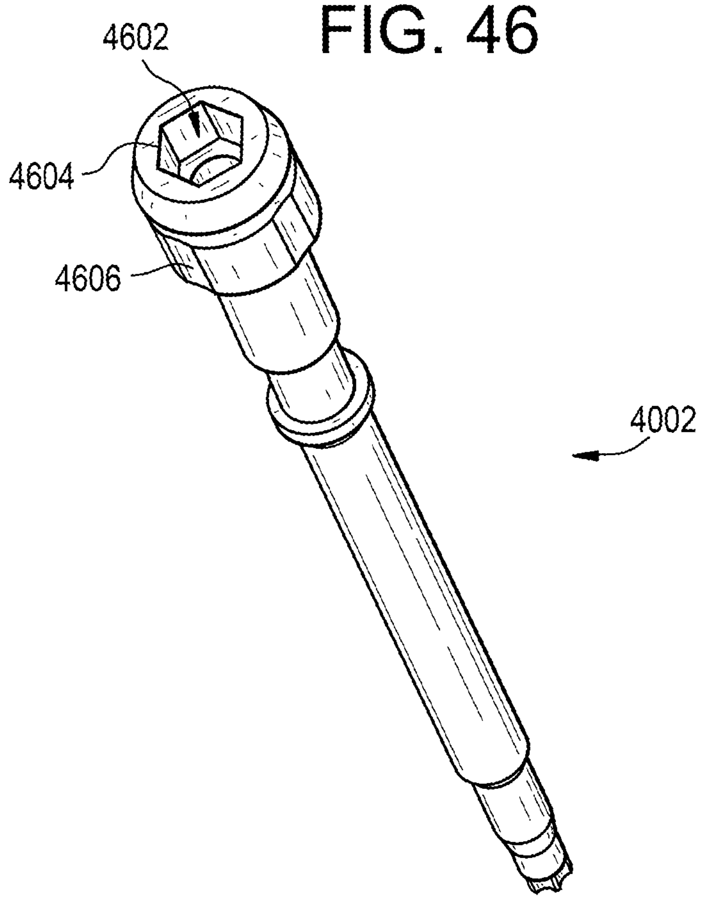
FIG. 46 is a rear perspective view of the bone screw driver shown in FIG. 40.
Figure 47:
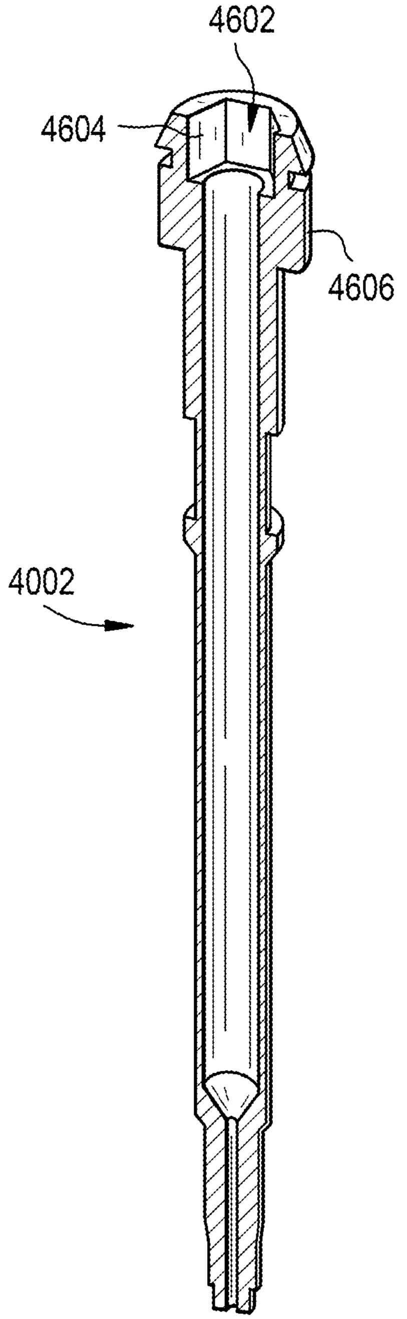
FIG. 47 is a longitudinal cross-sectional view of the bone screw driver shown in FIG. 46.

FIGS. 46 and 47 illustrate the driver 4002 in greater detail. The driver 4002 can be similar in many ways to the drivers described above. The driver 4002, however, can include a lumen 4602 having a proximal-most portion with one or more flat sidewall portions 4604. In addition, in some embodiments, a diameter of the lumen along the proximal-most portion with the one or more flat sidewall portions 4604 can be greater than a diameter along other portions of the lumen. The proximal-most portion of the lumen 4602 can be configured to receive, for example, the first portion 4304 of the protrusion of the driver adapter 4004 such that the two components can be coupled in a manner that allows transmission of torque between the two components (e.g., prevents relative rotation between the components along a longitudinal axis thereof). In addition, a portion of the lumen 4602 distal to the above-described proximal-most portion can be configured to receive the second portion 4308 of the protrusion 4202 of the driver adapter 4004 in some embodiments. Extending a length of a first or second portion of a protrusion 4202 into a complementary lumen of the driver 4002 can aid more precise alignment between the components. Further, in the illustrated embodiment a proximal body 4606 of the driver 4002 can have a more rounded outer surface profile, e.g., a cylindrical outer surface or a surface having small flat portions formed thereon. This is because the outer surface of the proximal body 4606 is not utilized to transmit torque between the driver adapter 4004 and the driver 4002.

Figure 48:
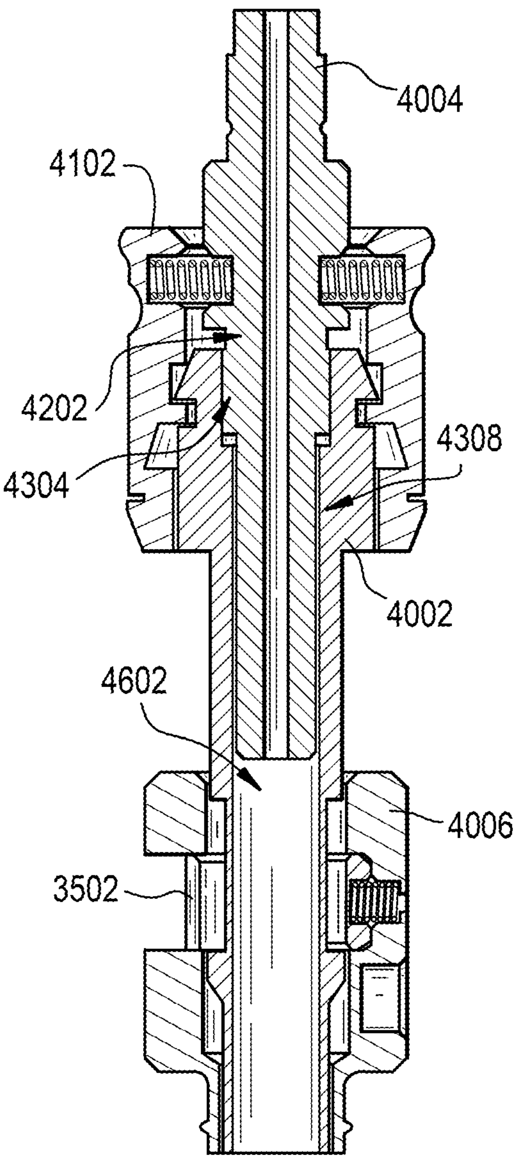
FIG. 48 is a longitudinal cross-sectional view of the assembly shown in FIG. 40.

FIG. 48 illustrates the coupling of the driver 4002 to the driver adapter 4004 and retaining sleeve 4006. This includes the lock 3502 that can selectively prevent axial separation of the driver 4002 and the retaining sleeve 4006, as well as the lock 4102 that can prevent axial separation of the driver and the driver adapter 4004. Also visible is the interaction between the protrusion 4202 formed on the driver adapter 4004 and the lumen 4602 of the driver 4002, including the proximal-most portion of the lumen that receives the first portion 4303 of the protrusion 4202 and a more distal portion of the lumen that receives the second portion 4308. Coupling the two components in this manner can allow improved alignment therebetween as well as the transmission of torque between the components (e.g., they can be locked against relative rotation with respect to one another).

The instruments disclosed herein can be constructed from any of a variety of known materials. Example materials include those which are suitable for use in surgical applications, including metals such as stainless steel, titanium, nickel, cobalt-chromium, or alloys and combinations thereof, polymers such as PEEK, ceramics, carbon fiber, and so forth. Further, various methods of manufacturing can be utilized, including 3D printing or other additive manufacturing techniques, as well as more conventional manufacturing techniques, including molding, stamping, casting, machining, etc.

The instruments and methods disclosed herein can be used in minimally-invasive surgery and/or open surgery. While the instruments and methods disclosed herein are generally described in the context of surgery on a human patient, it will be appreciated that the methods and instruments disclosed herein can be used in any of a variety of surgical procedures with any human or animal subject, or in non-surgical procedures.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Reconditioning of a device can utilize a variety of techniques for disassembly, cleaning/replacement, and reassembly. Use of such techniques, and the resulting reconditioned device, are all within the scope of the present application.

Various devices or components described herein can be processed before use in a surgical procedure. For example, a new or used device or component can be obtained and, if necessary, cleaned. The device or component can be sterilized. In one sterilization technique, the device or component can be placed in a closed and sealed container, such as a plastic or TYVEK bag. The container and its contents can be placed in a field of radiation that can penetrate the container, such as gamma radiation, x-rays, or high-energy electrons. The radiation can kill bacteria on the device or component and in the container. The sterilized device or component can be stored in the sterile container. The sealed container can keep the device or component sterile until it is opened in the medical facility. Other forms of sterilization are also possible, including beta or other forms of radiation, ethylene oxide, steam, or a liquid bath (e.g., cold soak). Certain forms of sterilization may be better suited to use with different devices or components, or portions thereof, due to the materials utilized, the presence of electrical components, etc.

In this disclosure, phrases such as “at least one of” or “one or more of” may occur followed by a conjunctive list of elements or features. The term “and/or” may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases “at least one of A and B,” “one or more of A and B,” and “A and/or B” are each intended to mean “A alone, B alone, or A and B together.” A similar interpretation is also intended for lists including three or more items. For example, the phrases “at least one of A, B, and C,” “one or more of A, B, and C,” and “A, B, and/or C” are each intended to mean “A alone, B alone, C alone, A and B together, A and C together, B and C together, or A and B and C together.” In addition, use of the term “based on,” is intended to mean, “based at least in part on,” such that an un-recited feature or element is also permissible.

Further features and advantages based on the above-described embodiments are possible and within the scope of the present disclosure. Accordingly, the disclosure is not to be limited by what has been particularly shown and described. All publications and references cited herein are incorporated by reference in their entirety, except for any definitions, subject matter disclaimers or disavowals, and except to the extent that the incorporated material is inconsistent with the express disclosure herein, in which case the language in this disclosure controls.

Examples of the above-described embodiments can include the following:

1. A surgical assembly, comprising:
   - a driver having a distal tip configured to couple with another component in a manner that prevents rotation therebetween, and a proximal driver body with a lumen extending from the proximal-most end of the driver to the distal-most end of the driver;
   - a driver adapter having a distal adapter body and a proximal torque-receiving end;
   - wherein the driver adapter is coupled to the driver such that a portion of the proximal driver body is received within a distal-facing cavity of the distal adapter body;
   - wherein the driver adapter is configured to impart rotational force to the driver and the distal adapter body includes a lock configured to prevent axial separation of the driver and the driver adapter.
2. The assembly of claim 1, wherein the driver adapter includes a lumen extending from a proximal-most end of the driver adapter to the distal-facing cavity.
3. The assembly of any of claims 1 to 2, wherein the lock includes one or more pivoting latches that interface with a groove formed on the driver.
4. The assembly of any of claims 1 to 3, wherein the driver includes one or more flats formed on the proximal driver body that interface with one or more flats formed on an interior surface of the distal-facing cavity of the driver adapter.
5. The assembly of any of claims 1 to 4, further comprising a retaining sleeve disposed over a portion of the driver.
6. The assembly of claim 5, wherein the retaining sleeve includes a threaded distal end configured to interface with a bone screw receiver head.
7. The assembly of any of claims 5 to 6, wherein the retaining sleeve includes a lock configured to prevent separation of the retaining sleeve and driver.
8. The assembly of any of claims 5 to 7, further comprising a second sleeve disposed over a portion of the retaining sleeve.
9. The assembly of claim 8, wherein the second sleeve includes a plurality of rigid extensions formed at a distal end thereof configured to be received between portions of a bone screw receiver head.
10. The assembly of any of claims 8 to 9, wherein the second sleeve includes a plurality of flexible extensions formed at a proximal end thereof configured to deflect and ride over one or more surface features formed on the retaining sleeve.
11. The assembly of any of claims 8 to 10, wherein the second sleeve is configured to move between a distal position, in which the second sleeve is locked against rotation relative to a bone screw receiver head coupled to the retaining sleeve, and a proximal position, in which the second sleeve can rotate relative to the bone screw receiver head coupled to the retaining sleeve.
12. The assembly of any of claims 1 to 11, further comprising a driver handle coupled to the proximal torque-receiving end of the driver adapter.
13. The assembly of any of claims 1 to 12, further comprising a surgical navigation array coupled to the driver adapter.
14. A surgical method, comprising:
   - inserting a driver through a lumen of a retaining sleeve such that a tip formed at a distal-most end of the driver interfaces with a drive feature formed on a shank of a bone screw assembly;
   - coupling the retaining sleeve to a receiver head of the bone screw assembly;
   - coupling a driver adapter to the driver such that a proximal portion of the driver is received within a distal-facing cavity of the driver adapter and the driver adapter is locked against axial separation from the driver; and rotating the driver adapter to impart corresponding rotation of the driver and the shank of the bone screw assembly.

15. The method of claim 14, wherein rotation of the driver and the shank of the bone screw assembly is relative to the retaining sleeve.

16. The method of any of claims 14 to 15, further comprising coupling a driver handle to a proximal end of the driver adapter.

17. The method of any of claims 14 to 16, further comprising locking the driver against axial separation from the retaining sleeve.

18. The method of any of claims 14 to 17, further comprising inserting the retaining sleeve through a lumen of a second sleeve.

19. The method of claim 18, wherein inserting the retaining sleeve through the lumen of the second sleeve is performed before coupling the retaining sleeve to the receiver head of the bone screw assembly.

20. The method of any of claims 18 to 19, further comprising moving the second sleeve between a distal position, in which the second sleeve is locked against rotation relative to the receiver head of the bone screw assembly, and a proximal position, in which the second sleeve can rotate relative to the receiver head of the bone screw assembly.

21. The method of any of claims 14 to 20, wherein the steps of coupling the retaining sleeve to the receiver head, inserting the driver through the lumen of the retaining sleeve, and coupling the driver adapter to the driver are performed outside of a surgical field.

22. The method of any of claims 14 to 21, further comprising:

separating the driver adapter from the driver;

coupling a bone cement delivery device to the driver; and delivering bone cement through the driver and the shank of the bone screw assembly.

23. A bone screw driver, comprising:

a distal tip;

a proximal body;

wherein a lumen extends from the proximal-most end of the bone screw driver to the distal-most end of the bone screw driver;

wherein the tip is formed at a distal-most end of the bone screw driver and is configured to interface with a bone screw to impart torque thereto;

wherein the proximal body includes opposed flats formed thereon configured to allow application of torque to the bone screw driver;

wherein the proximal body has a diameter greater than a distance between the opposed flats at a position distal to the opposed flats.

24. The device of claim 23, further comprising a coupling feature formed at a location proximal to the opposed flats, wherein the coupling feature is configured interface with a driver adapter in a manner that prevents axial separation of the bone screw driver and driver adapter.

25. The device of claim 24, wherein the coupling feature includes a groove formed around a circumference of the proximal body.

26. The device of any of claims 23 to 25, further comprising an intermediate portion extending between the distal tip and the proximal body portion, wherein the intermediate portion has a diameter less than a diameter of the proximal body portion.

27. The device of claim 26, further comprising a first shoulder formed along the intermediate portion and a second shoulder formed along the intermediate portion at a position distal to the first shoulder.

28. The device of claim 27, wherein the second shoulder includes a tapered distal-facing surface.

29. The device of any of claims 26 to 28, wherein the distal tip has a diameter less than that of the intermediate portion.

30. The device of any of claims 23 to 29, wherein the lumen includes at least one portion along its length with a tapering diameter.

31. The device of any of claims 23 to 30, wherein a proximal-most portion of the proximal body has a conical outer surface with a diameter that tapers toward the proximal-most end of the driver.

32. A bone screw driver adapter, comprising:

a distal adapter body;

a proximal torque-receiving end;

wherein the distal adapter body has a diameter greater than the proximal torque-receiving end;

wherein the distal adapter body defines a distal-facing cavity configured to receive a proximal portion of a bone screw driver;

wherein a distal-facing surface within the cavity includes a protrusion extending distally therefrom that is configured to be received within a lumen of the bone screw driver and impart torque thereto; and wherein the distal adapter body includes a lock configured to engage with the proximal portion of the bone screw driver when received within the cavity to prevent axial separation of the bone screw driver and the bone screw driver adapter.

33. The device of claim 32, wherein the proximal torque-receiving end includes one or more flats configured to allow application of torque to the bone screw driver adapter.

34. The device of any of claims 32 to 33, further comprising an intermediate portion extending between the distal adapter body and the proximal torque-receiving end, wherein the intermediate portion has a diameter less than a diameter of the distal adapter body.

35. The device of any of claims 32 to 34, wherein the bone screw driver adapter includes a lumen extending from a proximal-most end of the adapter to the distal-facing cavity.

36. The device of any of claims 32 to 35, wherein the lock includes one or more pivoting latches with a first end exposed along an outer surface of the distal adapter body and a second end extending into the distal-facing cavity.

37. The device of claim 36, wherein the one or more pivoting latches are biased to drive the second end radially inward within the distal-facing cavity.

38. The device of any of claims 32 to 37, further comprising a surgical navigation array mount disposed between the distal adapter body and the proximal torque-receiving end.

39. The device of any of claims 32 to 38, wherein the distal-facing cavity includes at least one opening formed therein that extends to an outer surface of the adapter body.

40. The device of any of claims 32 to 39, wherein the outer surface of the distal adapter body includes one or more flats formed thereon.

41. The device of any of claims 32 to 40, wherein the protrusion includes one or more flats formed thereon.

42. The device of claim 41, wherein the protrusion includes a first portion having the one or more flats formed thereon and a second portion extending distal to the first portion and having a diameter less than a diameter of the first portion.

43. A bone screw driver, comprising:

a distal tip;

a proximal body;

wherein a lumen extends from the proximal-most end of the bone screw driver to the distal-most end of the bone screw driver;

wherein the tip is formed at a distal-most end of the bone screw driver and is configured to interface with a bone screw to impart torque thereto;

wherein a proximal-most portion of the lumen includes one or more flat sidewall portions configured to allow application of torque to the bone screw driver.

44. The device of claim 43, wherein a diameter of the lumen is greatest along the proximal-most portion having the one or more flat sidewall portions.

What is claimed is:

1. A surgical assembly, comprising:

a driver having a distal tip configured to couple with another component in a manner that prevents rotation therebetween, and a proximal driver body with a lumen extending from the proximal-most end of the driver to the distal-most end of the driver;

a driver adapter having a distal adapter body and a proximal torque-receiving end;

wherein the driver adapter is coupled to the driver such that a portion of the proximal driver body is received within a distal-facing cavity of the distal adapter body;

wherein the driver adapter is configured to impart rotational force to the driver and the distal adapter body includes one or more pivoting latches that interface with a groove formed on the driver to prevent axial separation of the driver and the driver adapter.

2. The assembly of claim 1, wherein the driver adapter includes a lumen extending from a proximal-most end of the driver adapter to the distal-facing cavity.

3. The assembly of claim 1, wherein the driver includes one or more flats formed on the proximal driver body that interface with one or more flats formed on an interior surface of the distal-facing cavity of the driver adapter.

4. The assembly of claim 1, further comprising a retaining sleeve disposed over a portion of the driver.

5. The assembly of claim 4, wherein the retaining sleeve includes a threaded distal end configured to interface with a bone screw receiver head.

6. The assembly of claim 4, wherein the retaining sleeve includes a lock configured to prevent separation of the retaining sleeve and driver.

7. The assembly of claim 4, further comprising a second sleeve disposed over a portion of the retaining sleeve.

8. The assembly of claim 7, wherein the second sleeve includes a plurality of rigid extensions formed at a distal end thereof configured to be received between portions of a bone screw receiver head.

9. The assembly of claim 7, wherein the second sleeve includes a plurality of flexible extensions formed at a proximal end thereof configured to deflect and ride over one or more surface features formed on the retaining sleeve.

10. The assembly of claim 7, wherein the second sleeve is configured to move between a distal position, in which the second sleeve is locked against rotation relative to a bone screw receiver head coupled to the retaining sleeve, and a proximal position, in which the second sleeve can rotate relative to the bone screw receiver head coupled to the retaining sleeve.

11. The assembly of claim 1, further comprising a driver handle coupled to the proximal torque-receiving end of the driver adapter.

12. The assembly of claim 1, further comprising a surgical navigation array coupled to the driver adapter.

13. A surgical assembly, comprising:

a driver having a distal tip configured to couple with another component in a manner that prevents rotation therebetween, and a proximal driver body with a lumen extending from the proximal-most end of the driver to the distal-most end of the driver;

a driver adapter having a distal adapter body and a proximal torque-receiving end;

wherein the driver adapter is coupled to the driver such that a portion of the proximal driver body is received within a distal-facing cavity of the distal adapter body;

a retaining sleeve disposed over a portion of the driver; and a second sleeve disposed over a portion of the retaining sleeve and configured to selectively lock the second sleeve against rotation relative to a bone screw receiver head coupled to the retaining sleeve;

wherein the driver adapter is configured to impart rotational force to the driver and the distal adapter body includes a lock configured to prevent axial separation of the driver and the driver adapter.

14. The assembly of claim 13, wherein the second sleeve is locked against rotation relative to the bone screw receiver head when in a first position relative to the retaining sleeve and permits rotation relative to the bone screw receiver head when in a second position relative to the retaining sleeve that is proximal to the first position.

15. A surgical assembly, comprising:

a driver having a distal tip configured to couple with another component in a manner that prevents rotation therebetween, and a proximal driver body with a lumen extending from the proximal-most end of the driver to the distal-most end of the driver;

a driver adapter having a distal adapter body and a proximal torque-receiving end;

wherein the driver adapter is coupled to the driver such that a portion of the proximal driver body is received within a distal-facing cavity of the distal adapter body;

a retaining sleeve disposed over a portion of the driver; and a second sleeve disposed over a portion of the retaining sleeve, the second sleeve including a plurality of rigid extensions formed at a distal end thereof configured to be received between portions of a bone screw receiver head;

wherein the driver adapter is configured to impart rotational force to the driver and the distal adapter body includes a lock configured to prevent axial separation of the driver and the driver adapter.

16. A surgical assembly, comprising:

a driver having a distal tip configured to couple with another component in a manner that prevents rotation therebetween, and a proximal driver body with a lumen extending from the proximal-most end of the driver to the distal-most end of the driver;

a driver adapter having a distal adapter body and a proximal torque-receiving end;

wherein the driver adapter is coupled to the driver such that a portion of the proximal driver body is received within a distal-facing cavity of the distal adapter body;

a retaining sleeve disposed over a portion of the driver; and a second sleeve disposed over a portion of the retaining sleeve, the second sleeve including a plurality of flexible extensions formed at a proximal end thereof configured to deflect and ride over one or more surface features formed on the retaining sleeve;

wherein the driver adapter is configured to impart rotational force to the driver and the distal adapter body includes a lock configured to prevent axial separation of the driver and the driver adapter.

17. A surgical assembly, comprising:

a driver having a distal tip configured to couple with another component in a manner that prevents rotation therebetween, and a proximal driver body with a lumen extending from the proximal-most end of the driver to the distal-most end of the driver;

a driver adapter having a distal adapter body and a proximal torque-receiving end;

wherein the driver adapter is coupled to the driver such that a portion of the proximal driver body is received within a distal-facing cavity of the distal adapter body; and wherein a distal-facing surface within the distal-facing cavity includes a protrusion extending distally therefrom that is configured to be received within the lumen of the proximal driver body and impart torque thereto; and wherein the driver adapter is configured to impart rotational force to the driver and the distal adapter body includes a lock configured to prevent axial separation of the driver and the driver adapter.

18. The device of claim 17, wherein the protrusion includes one or more flats formed thereon.

19. The device of claim 18, wherein the protrusion includes a first portion having the one or more flats formed thereon and a second portion extending distal to the first portion and having a diameter less than a diameter of the first portion.

* * * * *